United States Patent [19]
Haynes et al.

[11] Patent Number: 5,998,173
[45] Date of Patent: Dec. 7, 1999

[54] PROCESS FOR PRODUCING N-ACETYL-D-GLUCOSAMINE

[75] Inventors: Charles A. Haynes; Pedro Aloise; Aimee Louise Creagh, all of Vancouver, Canada

[73] Assignee: The University of Bristish Columbia, Vancouver, Canada

[21] Appl. No.: 08/603,360

[22] Filed: Feb. 20, 1996

[51] Int. Cl.$^6$ .................................................. C12P 19/26
[52] U.S. Cl. ........................ 435/84; 435/911; 435/945; 435/822; 435/881
[58] Field of Search ............................. 435/84, 881, 822, 435/911, 545

[56] References Cited

U.S. PATENT DOCUMENTS

| | | | |
|---|---|---|---|
| 5,061,627 | 10/1991 | Olsen et al. | 435/183 |
| 5,262,310 | 11/1993 | Karube et al. | 435/85 |

FOREIGN PATENT DOCUMENTS

| | | |
|---|---|---|
| 63-27393 | 11/1988 | Japan . |
| 1-104158 | 4/1989 | Japan . |
| 1291793 | 11/1989 | Japan . |
| 2031685 | 2/1990 | Japan . |
| 3094697 | 4/1991 | Japan . |
| 5007496 | 1/1993 | Japan . |
| 93004067 | 1/1993 | Japan . |
| 5084087 | 4/1993 | Japan . |
| 93033037 | 5/1993 | Japan . |
| 94032605 | 5/1994 | Japan . |
| WO 94/24288 | 10/1994 | WIPO . |

OTHER PUBLICATIONS

Monreal et al., "The Chitinase of Serratia marcescens", Can. J. Microbiology, 1969, vol. 15, pp. 689–696.

Vyas et al., "Cnitinase production by Myrothecium verrucaria and its significance for fungal mycelia degradation", J. Gen. Appl. Microbiol. 1989, vol. 35, pp. 343–350.

Neugebauer et al., "Chitinolytic properties of Streptomyces lividans", Arch. Microbiol., 1991, vol. 156, pp. 192–197.

Cosio et al. "Bioconversion of shellfish chitin waste: waste pretreatment, enzyme production, process design and econoic analysis", Journal of Food Science, 1982, vol. 47, pp. 901–905.

Biotechnology. Edited by H.J. Rehm and G. Reed, VCH, 1985, vol. 2, "Fundamentals of Biochemical Engineering", pp. 302–309.

Biotechnology. Edited by H.J. Rehm and G. Reed, VCH, 1987, vol. 7a, "Enzyme technology", pp. 527–531.

Chemical Abstract No. 115:230433, 1991.

*Primary Examiner*—Sandra E. Saucier
*Assistant Examiner*—Vera Afremova
*Attorney, Agent, or Firm*—Oyen Wiggs Green & Mutala

[57] ABSTRACT

This invention pertains to a novel process for directly producing N-acetyl-D-glucosamine from chitin. More particularly, this invention pertains to a novel process for producing N-acetyl-D-glucosamine utilizing an ensemble of the chitinase family of enzymes to hydrolyze chitin of crustacea shells. The invention includes a process for producing N-acetyl-D-glucosamine by enzymatically hydrolyzing chitin with an ensemble of chitinolytic enzymes, including chitinase and chitobiase. In particular, using a two-stage chitin-hydrolysis reactor.

24 Claims, 15 Drawing Sheets

- ●— Hammer-milled (≥ 450 μm)
- ■— Ball-milled (180-250μm)
- ▲— Steam-Exploded balled-milled (180 to 250 μm)
- -✕- Steam-Exploded (0.01% acid) balled-milled (180 to 250 μm)
- -+-- Dimethylacettimide-treated (180 to 250 μm)

PROCESS FOR PRODUCING N-ACETYL-D-GLUCOSAMINE

FIELD OF THE INVENTION

This invention pertains to a novel process for directly producing N-acetyl-D-glucosamine from chitin. More particularly, this invention pertains to a novel economical, high efficiency process for producing N-acetyl-D-glucosamine utilizing an ensemble of the chitinase family of enzymes to hydrolyze chitin found in the shells of crustacea.

BACKGROUND OF THE INVENTION

In recent years, it has been discovered that N-acetyl-D-glucosamine is a valuable pharmacological agent in the treatment of a wide variety of ailments. N-acetyl-D-glucosamine does not have any established negative side effects. Rather, since it occupies an important place in protein synthesis, it has a positive effect on tissue regeneration. N-acetyl-D-glucosamine has therapeutic potential in the treatment of a wide variety of diseases including gastritis, food allergies, inflammatory bowel disease (IBD) and diverticulitis. N-acetyl-D-glucosamine is a valuable and important component of protein synthesis in the animal body.

Currently, N-acetyl-D-glucosamine is not widely available in the marketplace and is expensive. To date, N-acetyl-D-glucosamine in commercial quantities is prepared by a United States company which utilizes a process that is based on acid hydrolysis of crude chitin. This results in deacetylation of N-acetyl-D-glucosamine units to form glucosamine. The glucosamine is isolated and re-acetylated to N-acetyl-D-glucosamine using an organic acetylating reagent such as acetic anhydride.

Chitin, which is a major component of the exoskeleton of insects and shellfish, is a $\beta$ 1,4 linked unbranched polymer composed almost entirely of amino sugars, specifically N-acetyl-D-glucosamine, and is a natural substrate for the manufacture of this compound. N-acetyl-D-glucosamine is a natural substance, has a somewhat pleasant sweet taste, is non-toxic and dissolves easily in water and bodily fluids.

N-acetyl-D-glucosamine, specifically 2-acetamido-2-deoxy-D-glucose, belongs to a larger class of amino sugars which serve a number of important functions and are localized in many areas of the human biosystem. N-acetyl-D-glucosamine is a key amino sugar which is made in the body of all animals from glucose, also called blood sugar. Complex (polymeric) carbohydrates containing N-acetyl glucosamine, referred to as glycosaminoglycans, become associated with or attached to proteins to form a class of compounds generally referred to as proteoglycans. N-acetyl-D-glucosamine is part of the makeup of body tissues and blood vessels, and the protective coverings over the digestive, respiratory and genitourinary organs. In this capacity, it is involved in the regulation of what enters and leaves the body and the movement of substances into and between cells of the body. The biochemical processes involved in amino sugar synthesis and utilization occur in all cells and are fairly well understood.

Amino sugars make up over half the glycosamino-glycans of interstitial tissue that fills the spaces between cells and forms the cellular "glue" that binds cells together. This material is a gel-like matrix of collagen protein and glycosamino-glycans, holding cells in place and regulating those substances which pass between cells.

Amino sugars are also a major constituent of basement membranes; the tough, thin sheets which surround blood vessels and various tissues. These tissues control the nutrients and waste products that cross the cell membranes, supporting tissue structures and influence cell growth.

Certain disease processes appear to be related to abnormalities in the formation and utilization of amino sugars which are natural constituents of many tissues in the body. Since amino sugars are vital components for many tissues it is easy to rationalize that a reduction in the availability of amino sugars would lead to abnormal cellular functions. Cell membranes, intercellular fluids, cell regeneration and overall tissue metabolism could all be affected. A deficiency in this fundamental building block in the body could lead to a variety of medical disorders.

In U.S. Pat. No. 5,262,310, granted Nov. 16, 1993, Isao Karube et al., discloses and claims a process wherein chitin-containing material is heat-treated in organic solvent, or in a solvent with water, and then $\beta$-1,4 glycoside decomposing enzyme is added for decomposing the chitin-containing material by enzyme reaction. Alternatively, chitin-containing material is ultrasonicated in organic solvent or in the solvent with water, and then chitin-containing material is decomposed by enzyme reaction of $\beta$-1,4 glycoside decomposing enzyme. Further, chitin-containing material is exposed in the solution containing urea and/or surfactant, and then chitin-containing material is let co-exist with $\beta$-1,4 glycoside decomposing enzyme under the presence or non-presence of urea and/or surfactant for decomposing chitin-containing material. In a further variation, at the time of exposing chitin-containing material in the solution containing urea and/or surfactant, the solution is heated and the $\beta$-1,4 glycoside decomposing enzyme is added for decomposing chitin-containing material. Specifically, the process comprises an enzymatic method of decomposing chitin, comprising: mixing the chitin with an organic solvent, thereby creating a chitin and solvent mixture, wherein the mixing step comprises ultrasonicating the chitin and solvent mixture; heating the chitin and solvent mixture; and adding $\beta$-1,4 glycosidase to the mixture.

A number of Japanese patents disclose various methods of treating chitin, or chitin derivatives, with chitinase enzymes.

Japanese Patent No. 5,084,087, Apr. 6, 1993, discloses the release of N-acetyl-D-glucosamine by treating a polysaccharide with acid chitinase induced with ethylene in azuki bean plant.

Japanese Patent No. 5,007,496, Jan. 19, 1993, discloses the preparation of the oligosugar (high polymerized heterooligo sugar of glucosamine and N-acetyl glucosamine, and monooligosugar of glucosamine) by hydrolysis of the partially deacetylated chitin by chitinase. The preparation is carried out in a dialysis membrane, by dialysis. Cation ion exchange chromatography is placed outside the membrane. The chitin is obtained from crustacea or tricomonus.

Japanese Patent No. 3,094,697, Apr. 19, 1991, discloses a method comprising completely decomposing chitin or chitosan into their structural units, N-acetyl glucosamine and glucosamine using enzymes, and then determining the monosaccharide. The deacetylation degree of chitin and chitosan can be measured readily with high accuracy. The enzyme preferably includes exo type $\beta$-D-glucosoaminidase, $\beta$-N-acetylhexosaminidase, chitosanase, chitinase, lysozyme, etc. The measurement of N-acetyl glucosamine and glucosamine is conducted using high speed liquid chromatography, colorimetory, etc.

Japanese Patent No. 2,031,685, Feb. 1, 1990, discloses a method of producing monosaccharides characterized by (a) treating starch and/or its hydrolyzate with endo-form polysaccharide-decomposing enzyme and (b) accumulating monosaccharide with high concentration. As polysaccharide and/or its hydrolyzate starch and/or its hydrolyzate, xylan and/or its hydrolyzate, mannan and/or its hydrolyzate, chitin and/or its hydrolyzate and galactan and its hydrolyzate can be used and as polysaccharide-decomposing enzyme, alpha-amylase, xylanase, mannase, chitinase and galactanase can be used respectively. The monosaccharide formed by the above combination is glucose, xylose, mannose, N-acetyl glucosamine or galactose.

Japanese Patent No. 1,291,793, Nov. 24, 1989, discloses endo-type chitinase production by cultivation of trichoderma AF6-T8 in liquid medium containing colloidal or fine particles, used to produce acetyl glucosamine.

Japanese Patent No. 93,004,067, Jan. 19, 1993, discloses the production of chitosan, N-acetyl glucosamine, etc., by cultivating Flavobacterium MP-1C and/or Pseudomonas MP-1D strains in the presence of crustaceae shells. The chitin in the shell can purportedly be effectively decomposed and chitosan, N-acetyl-glucosamine, etc. can be prepared. Chitin-decomposing enzymes such as chitinase, chitobiase, chitin deacetylase and chitosanase can also be recovered by fractionating means such as ultrafiltration, etc.

Japanese Patent No. 93,033,037, May 18, 1993, discloses N-acetyl-D-glucosamine preparation by hydrolyzing chitin to N-acetyl-chito-oligosaccharide, and then further hydrolyzing with an enzyme. The method is characterized by (a) hydrolyzing chitin partially with acid and (b) treating the thus obtained mixture containing N-acetylchito-oligosaccharides with the enzyme which hydrolyzes N-acetylchito-oligosaccharide as substrate. The lysozyme is chitinase, chitobiase, etc. They decompose N-acetyl chito-oligosaccharide to N-acetyl-D-glucosamine.

Japanese Patent No. 94,032,605, May 2, 1994, discloses chitinase-producing Streptomyces microorganism, used for the production of chitin degradation products. A microorganism of Streptomyces produces chitinase. Preferable strains are Streptomyces sp. KE-406 (FERM P-8642), Streptomyces sp. KE-902 (FERM P-8643) and Streptomyces sp. KE-3332 (FERM P-8644). They are all isolated from soil. Chitinase with high activity is produced by culture of a strain of Streptomyces. By using the chitinase, chitinase degradation products, e.g. N-acetyl glucosamine and chitooligosaccharide are produced efficiently.

Chemical Abstract 115:230433 discloses that chitinolytic enzymes containing chitinase and β-N-acetyl-hexosaminidase from *Nocardia orientalis* IFO 12806 were immobilized on various carriers by different methods for the continuous production of N-acetyl glucosamine. The immobilized enzyme containing both enzymes prepared by physical adsorption to tannin-chitosan was very useful for N-acetyl glucosamine production.

SUMMARY OF THE INVENTION

We have discovered a process whereby N-acetyl-D-glucosamine can be produced directly from chitin. With our process, it is not necessary to proceed through an intermediate glucosamine step. Thus, not only does our process enable N-acetyl-D-glucosamine to be produced at considerably reduced cost, but the process is environmentally acceptable and friendly because organic solvents are not required (except for a re-crystallization step with alcohol).

The invention in one aspect is directed to a process for producing N-acetyl-D-glucosamine (2-acetamido-2-deoxy-D-glucose) which comprises enzymatically hydrolyzing chitin with an ensemble of chitinolytic enzymes. The ensemble of chitinolytic enzymes can contain at least one chitinase and one chitobiase produced and secreted from either a procaryotic or eucaryotic organism. The chitinase can be either an endo- or exo-β-1,4-glycanohydrolases (EC 3.2.1.14), and the chitobiase can be a β-n-acetyl-glucosaminidase (HC 3.2.1.30) (known also as an acetylamino deoxyglucohydrolase (BC 3.2.1.29)), or a β-N-acetyl-hexosaminidase (EC 3.2.1.52).

The chitin can be obtained from the exoskeletons of crustacea. The crustacea can be krill, shrimp, crab and lobster, or other suitable crustacea. The chitinase and chitobiase enzymes which comprise the ensemble of chitinolytic enzymes can be obtained by fermenting chitin obtained from the exoskeletons of crustacea with a selected organism to induce the production of at least one chitinase and one chitobiase.

The procaryotic organism can be a bacterial cell line selected from the group consisting of *Serratia marcescens*, *Streptomyces lividans* and *Enterobacter liquefaciens*. The eucaryotic organism can be a fungal cell line selected from the group consisting of *Trichoderma harzanum* and *Myrothecium verrucaria*.

The invention in another aspect is directed to a process for the production of an ensemble of chitinolytic enzymes which comprises: (a) introducing a chitin-containing substance into a fermentor or culturing vessel; (b) generating a culture by introducing an inoculum of a procaryotic or eucaryotic organism into the fermentor or culturing vessel to induce organism expansion and production of enzymes having chitinase or chitobiase activity; and (c) recovering of the ensemble of chitin-degrading enzymes and chitobiose-degrading enzymes from the culture.

The chitinase-degrading enzymes and chitobiase-degrading enzymes in the ensemble can be contained in an extracellular fluid. The enzymes can be recovered by passing the culture through a membrane separator or through a centrifuge to yield a filtrate solution containing the ensemble of chitinolytic enzymes which can contain at least one chitinase and one chitobiase. Retantate from the membrane separator can be recycled back to the fermentor or culture vessel.

The invention in a further aspect is directed to a process from the production of N-acetyl-glucosamine comprising: (a) introducing a chitin-containing solid substrate, a defined carbohydrate-free media, and an organism which produces chitin-degrading and chitobiose-degrading enzymes when grown on chitin into a fermentor or culture vessel; (b) producing a culture by applying a culturing protocol which induces the organism to produce and secrete an ensemble of chitinolytic enzymes containing at least one chitin-degrading enzyme (chitinase) and one chitobiose-degrading enzyme (chitobiase); (c) separating the ensemble of chitinolytic enzymes from other components of the culture; (d) mechanically or physico-chemically treating chitin-containing solids; (e) introducing the ensemble of chitinolytic enzymes of step (c) and the chitin-containing solids of step (d) into a chitin-hydrolysis reactor where the chitin component of a solid is hydrolyzed to N-acetyl-D-glucosamine; (f) separating the ensemble of chitinolytic enzymes and N-acetyl-D-glucosamine into a filtrate stream containing N-acetyl-D-glucosamine and a retentate stream containing the chitinolytic enzymes.

The chitinolytic enzymes comprising chitinase(s) and chitobiase(s) can be recycled to the chitin-hydrolysis reactor. The chitin-hydrolysis reactor of step (e) can be a sequential two-stage reactor. The two-stage reactor can comprise a single unit in which a bottom portion of the working volume of the reactor can contain a packed-bed of chitin-containing solid through which an enzyme-containing mobile phase passes and wherein an upper portion is a solids-free aqueous solution containing chitobiose-degrading enzyme(s).

The two-stage reactor can also comprise two sequential reactors in which the first reactor can contain a packed-bed of chitin-containing solid through which an enzyme-containing mobile phase passes and wherein the second reactor can be a stirred tank containing a solids-free aqueous solution which is catalyzed by one or more chitobiose-degrading enzymes.

The enzyme ensemble feed solution can be introduced into the bottom of the packed bed. The two-stage reactor can be maintained at a pH of between about 5.5 and 7.5, and an isothermal temperature of between about 30° C. and 55° C. The chitin-containing solids can be pretreated to increase external availability of chitin. The pretreatment can comprise ball-milling or hammer-milling or steam explosion or steam expansion of chitin-containing solids.

The chitin-hydrolysis reactor of step (e) can be a semi-fluidized bed reactor. The ensemble of chitinolytic enzymes of process step (c) can be separated by a membrane filtration process. The chitinolytic enzymes and N-acetyl D-glucosamine can be separated into a filtrate stream by an ultrafiltration process.

The invention in a further embodiment is directed to a process for the production of N-acetyl-glucosamine comprising: (a) introducing a chitin-containing solid substrate, a defined carbohydrate-free media, and an organism which produces chitin-degrading and chitobiose-degrading enzymes when grown on chitin into a fermentor or culture vessel; (b) producing a culture by applying a culturing protocol which induces the organism to produce and secrete an ensemble of chitinolytic enzymes containing at least one chitin-degrading enzyme (chitinase) and one chitobiose-degrading (chitobiase) enzyme; (c) separating the ensemble of chitinolytic enzymes from other components of the culture; (d) introducing the ensemble of chitinolytic enzymes and the chitin-containing solids into a chitin-hydrolysis reactor where the chitin component of the solids is hydrolyzed to N-acetyl-D-glucosamine; (e) separating the ensemble of chitinolytic enzymes and N-acetyl-D-glucosamine into a filtrate stream containing N-acetyl-D-glucosamine and a retentate stream containing the ensemble of chitinolytic enzymes.

The invention in yet another aspect is directed to a process for the production of N-acetyl-D-glucosamine comprising: (a) producing a chitinolytic ensemble of enzymes using a fermentation protocol according to the invention; (b) partially purifying of the chitinolytic enzyme ensemble using a two-stage filtration or centrifugation system which allows chitin nutrients and cell mass to be recycled to a fermentor; (c) delivering and recycling the partially purified chitinolytic enzyme ensemble throughout the system; (d) introducing the enzymes and chitin containing solids into a chitin-hydrolysis bioreactor which contains a pretreated chitin-containing solid substrate and into which is fed an aqueous solution containing the partially purified chitinolytic enzyme ensemble; and (e) separating the N-acetyl-D-glucosamine product from the enzymes and high-molecular-weight oligosaccharides in the bioreactor exit/recycle stream by a cross-flow ultrafiltration system.

The chitinase and chitobiase enzymes can be recycled to the chitin-hydrolysis bioreactor. The chitin-hydrolysis bioreactor can be operated in one of at least two basic configurations: (a) a single column containing a packed bed of chitin-containing substrate in the lower portion and chitin-free (solids free) solution in the upper portion where the enzyme feed solution enters the bottom of the reactor and the product stream exits from the top, or (b) a sequential modular design in which the enzyme feed solution is first passed through a packed bed of chitin-containing substrate and the components which exit the column are then fed into a stirred tank reactor which yields the N-acetyl-D-glucosamine product. In the latter configuration, the enzyme feed solution can be introduced into either the bottom or the top of the packed bed. The reactor assembly can be maintained at a temperature between about 25° C. and 55° C. and a pH between about pH 5.5 and 8.

BRIEF DESCRIPTION OF THE DRAWINGS

In drawings which illustrate specific embodiments of the invention, but which should not be construed as restricting the spirit or scope of the invention in any way.

DETAILED DESCRIPTION OF THE INVENTION

Figure 1A:
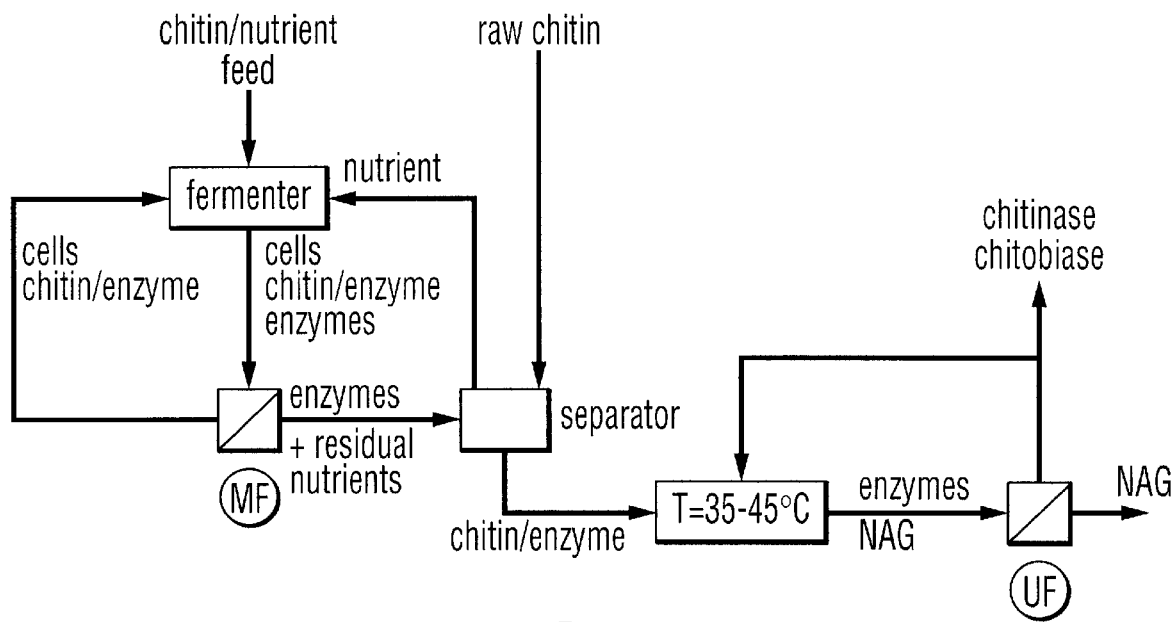
FIG. 1a and 1b illustrate schematic flow sheets of two alternative ways to practice the process of the invention for the production of N-acetyl-D-glucosamine from chitin containing solids.

A new process is described for the economical production of N-acetyl-D-glucosamine (NAG) by enzymatic hydrolysis of chitin by chitinolytic enzymes chitinase (chitin glycanohydrolase, EC 3.2.1.14) and chitobiase (acetylaminodeoxyglucohydrolase, EC 3.2.1.29) produced and secreted from bacterial cell lines.

This new invention involving N-acetyl-D-glucosamine production technology utilizes the abundance and low cost of chitin in nature. Chitin is a β-1,4-linked unbranched polymer composed primarily of N-acetyl-D-glucosamine. It is the second most abundant polymer (after cellulose) occurring in nature. Like cellulose, chitin is a structural polysaccharide whose natural sources include the exoskeletons of arthropods and the cell walls of many fungi. The primary commercial source of chitin is crab and shrimp shells; some global estimates of the total chitin content in shellfish waste are in the range of $1.2 \times 10^5$ metric tons per annum. In British Columbia, shrimp-shell waste per annum is estimated at 10,000 metric tons. Most of this chitinaceous waste is currently land-filled after steam sterilization. (In contrast, Japan is estimated to annually produce and process about $10^3$ mg of chitin for industrial use.)

The new process of the invention provides an economically viable alternative to current environmentally-unattractive chitinaceous-waste disposal procedures: bioconversion of shrimp-shell and crab-shell waste (for which provincial sterilization and land-filling costs are substantial) to N-acetyl-D-glucosamine, a moderately high-value therapeutic with a large potential world market.

Because of its inherently mild operating conditions, enzymatic hydrolysis of chitin is an attractive method for producing N-acetyl-D-glucosamine from chitinaceous waste. Microorganisms use a consortium of lytic enzymes to convert chitin to N-acetyl-D-glucosamine. The dimer, chitobiose, can be obtained by the action of exoand endo-chitinases on chitin; chitobiase then cleaves chitobiase to give two molecules of N-acetyl-D-glucosamine. The specificity of these enzymes ensures that N-acetyl-D-glucosamine is the ultimate hydrolysis product. An attractive feature of this bioprocess is the potential for additional profits through sale of purified chitinase and chitobiase, which are produced and secreted by the (chosen) microorganism in the presence of chitin. Natural sources of chitinases include snails, crustacea, insects, vertebrates, and bean seeds. However, the most convenient sources of chitinases, from a processing point of view, are microorganisms.

PROCESS

Historically, progress in chitinase research has been intimately linked with advances in cellulase research. As with the chitinases, the cellulases often act synergistically and become strongly adsorbed to their insoluble substrate as a precursor to hydrolysis of cellulose to soluble sugars (Muzzarelli, 1985). As a result, many of the tools and concepts used in the development of this invention of a process for N-acetyl-D-glucosamine production are drawn from earlier technologies, particularly those of Wilke et al. (Cysewski and Wilke, 1976; Wilke et al., 1976), utilizing the cellulase ensemble of hydrolytic enzymes for soluble sugar production. Additional concepts were drawn from the process proposed by Cosio et al. (1982) for the production of single-cell protein and ethanol from bioconversion of shellfish waste.

Figure 1B:
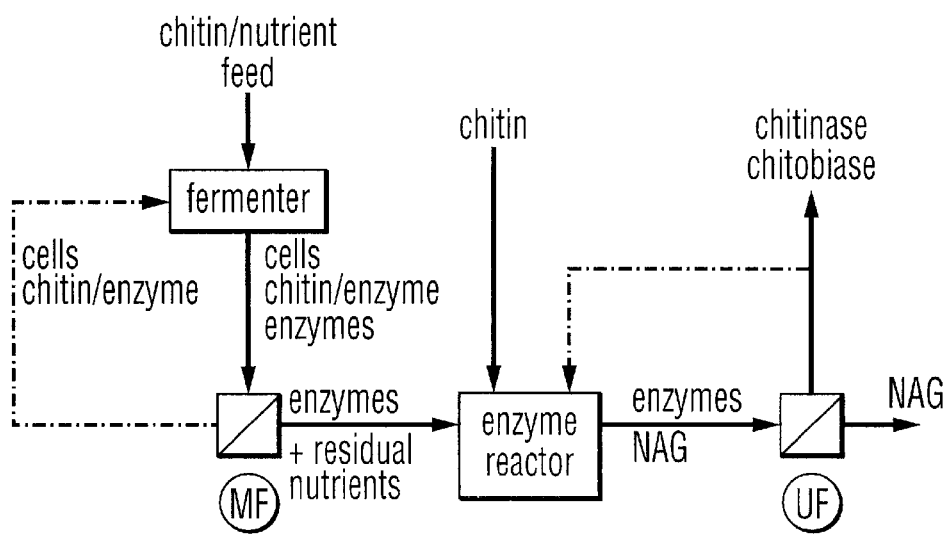

Two alternative forms of the process of the invention for producing N-acetyl-D-glucosamine from chitin are illustrated in the schematic flowsheets of FIGS 1a and 1b. An aliquot of shellfish exoskeleton or chitin is fed as a carbon source (and inducing agent) to a fermentor containing an inoculum of a selected chitinase-producing organism in exponential-phase growth. The introduction of chitin to the cell suspension induces production of an ensemble of two or more chitinases and chitobiase, which are secreted by the growing cells to the extracellular fluid. The chitin-degrading enzymes are recovered from the fermentation broth containing cells, chitin containing particles, the chitinolytic enzyme ensemble (chitobiase and at least two chitinases), a small concentration of N-acetyl-D-glucosamine, and oligomers of N-acetyl-D-glucosamine by passing the broth through either a membrane separator or a continuous centrifuge to yield a solution containing chitinolytic enzyme ensemble in the filtrate. The retentate containing viable cells and chitin may be recycled to the fermentor for further cell growth, and chitinolytic enzyme production. The retentate will also contain a residual amount of enzyme since adsorption of chitinase enzymes to chitin is the initial step in the hydrolysis reaction.

The chitinolytic enzyme containing filtrate solution may then be concentrated and further purified by one of the following methods: (a) membrane ultrafiltration where the nominal pore diameter of the membrane is sufficiently small to retain each enzyme in the chitinolytic enzyme ensemble, or (b) mixing the crude chitinolytic enzyme containing filtrate solution with an aqueous chitin dispersion or slurry in a solid-liquid separator fixed at a temperature low enough that the free enzymes bind to the chitin but do not hydrolyze it to any appreciable extent. Evidence that chitinases bind to chitin but do not hydrolyze it appreciably at low temperatures has been provided by Cabib[10] and through additional results from the applicants' laboratory. In method (b), the solid chitin/enzyme complex is settled, separated from the residual nutrient solution, washed, and then fed to a chitin-hydrolysis bioreactor where the chitin is enzymatically hydrolyzed by each chitinase and then by chitobiase to produce N-acetyl-D-glucosamine.

Figure 2A:
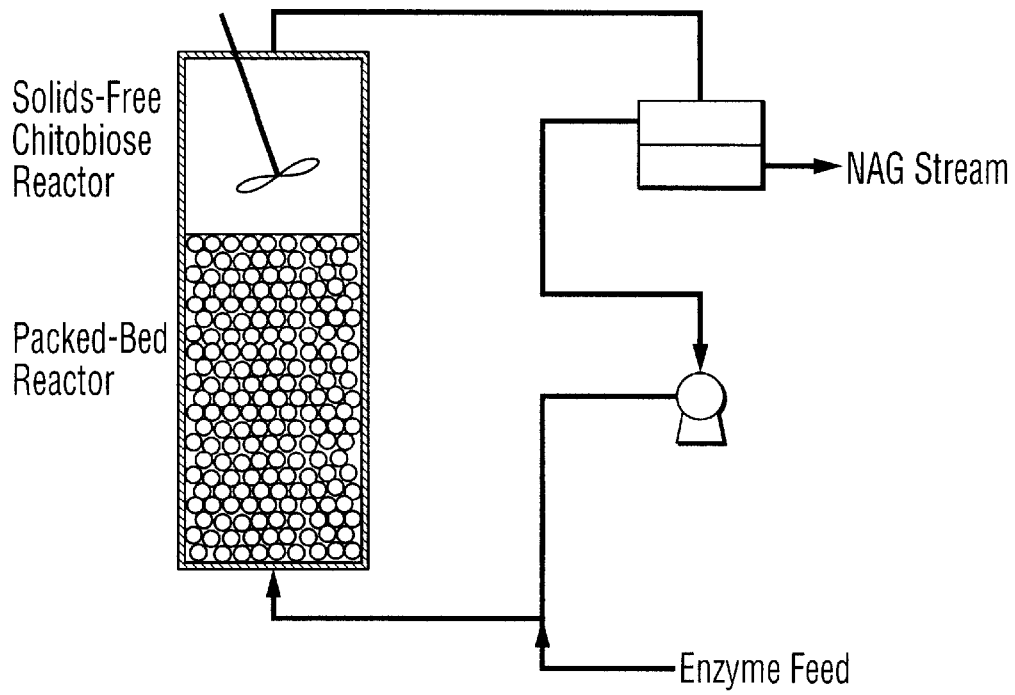
FIG. 2a illustrates a schematic depiction of a bed packed chitin-hydrolysis bioreactor.
Figure 2B:
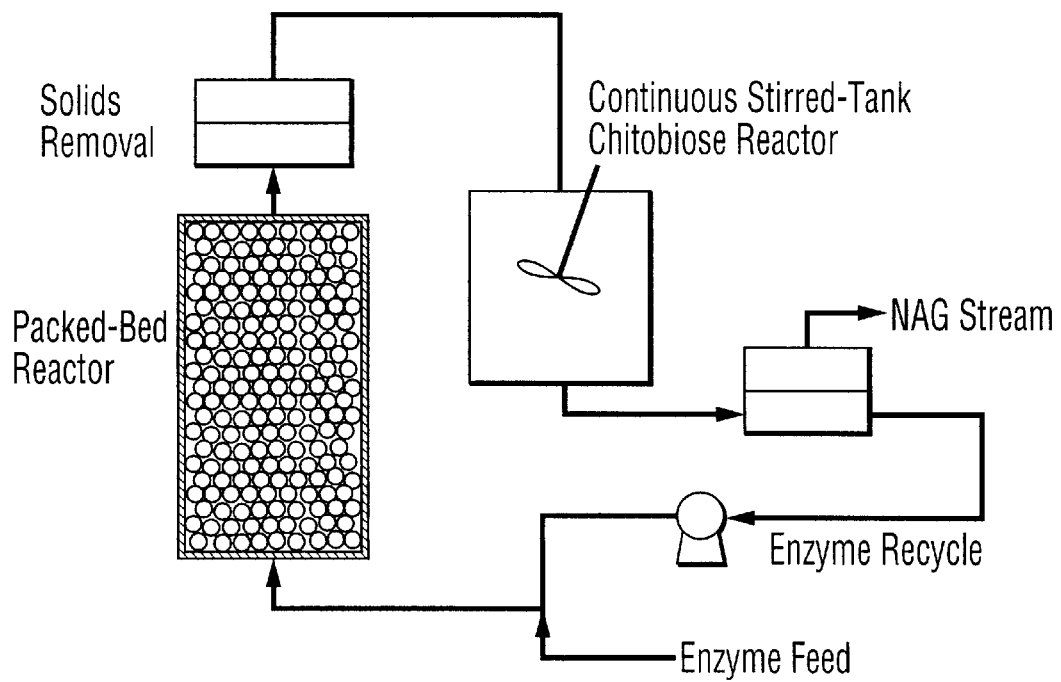
FIG. 2b illustrates a schematic depiction of a continuous stirred-tank reactor.

For the version of the invented process illustrated in FIG. 1a, where the chitinolytic ensemble of enzymes is concentrated and further purified by membrane ultrafiltration, the concentrated solution containing the chitinolytic enzyme ensemble may then be introduced into either of the chitin-hydrolysis bioreactor configurations shown in FIGS. 2a or 2b. In either configuration, the enzyme solution first passes through a packed bed of chitin onto which each chitinase enzyme adsorbs through a binding reaction between the insoluble chitin and a chitin binding domain found on either the N-terminus or C-terminus of the enzyme. Chitobiase, which is not a chitinase and is not known to contain a chitin binding domain, does not bind the solid (chitin-containing) phase and passes through the packed bed along with the solvent. Thus, the packed-bed reactor becomes progressively enriched in chitinase enzymes as the chitinolytic-enzyme-ensemble feed solution is passed through the column. The bound and free chitinases within the volume of the packed bed catalyse the hydrolysis of the chitin component of the insoluble particles to soluble low-molecular-weight oligosaccharides of N-acetyl-D-glucosamine, which are then transported out of the bed by the mobile phase.

The mobile-phase fluid exiting the packed-bed (portion of) the reactor is enriched in chitobiase, which does not bind to the solid-phase of the packed bed, and contains a mixture of N-acetyl-D-glucosamine and soluble low-molecular-weight oligomers of N-acetyl-D-glucosamine. The homogeneous chitobiase-enriched aqueous-phase component of the bioreactor, which may either be a free-volume continuation of the packed-bed reactor (FIG. 2a) or a separate continuous stirred-tank reactor (FIG. 2b), provides the necessary residence time for the excess of chitobiase to catalyze the complete hydrolysis of the soluble oligosaccharides to N-acetyl-D-glucosamine. This novel reactor configuration offers a number of distinct advantages. Chitinase activity is noncompetitively inhibited by the end-product N-acetyl-D-glucosamine. The relatively low concentration of chitobiase in the packed-bed portion of the reactor ensures that N-acetyl-D-glucosamine are low and production rates of soluble oligosaccharides are high in the packed bed. The relatively high concentration of chitobiase in the second homogeneous aqueous-phase portion of the reactor then ensures that all of the soluble oligosaccharides exiting the packed bed are converted to N-acetyl-D-glucosamine. As a result, both N-acetyl-D-glucosamine production rates and yields are significantly higher in the invented process than in any other process tested.

Final separation of the N-acetyl-D-glucosamine product from the chitinolytic enzymes (chitobiase and all chitinases) is achieved by cross-flow membrane ultrafiltration designed so that the N-acetyl-D-glucosamine exits with the filtrate and all of the enzymes are retained. To facilitate further production of N-acetyl-D-glucosamine, a portion of the enzyme ensemble is recycled to the inlet of the chitin-hydrolysis bioreactor; the remainder is isolated by a precipitating agent, which may be ammonium sulfate, to give a commercial-grade preparation of the chitinase ensemble of enzymes.

The process outlined in FIG. 1a involves five essential unit operations: (1) the fermention system required for both cell growth and production of the chitinolytic enzyme ensemble; (2) the chitinolytic-enzyme containing supernatant recovery system, which may involve filtration, centrifugation and/or adsorption; (3) physical and novel thermochemical processes for pretreatment of chitin-containing substrates to improve chitin exposure and hydrolysis rates; (4) the two-stage chitin-hydrolysis reactor; and (5) the final purification system providing N-acetyl-D-glucosamine and a commercial-grade preparation of the chitinase ensemble of enzymes. Examples illustrating the unique features of these unit operations which distinguish the applicants' N-acetyl-D-glucosamine production technology from any related technologies are provided below.

(1) Defined Fed-Batch Fermentation of Chitinase-Producing Bacteria Using Chitin or Crustacea Exoskeleton as the Sole Carbon Source:

A number of bacteria, including *Serratia marcescens*[19] and *Streptomyces lividans*[20], and fungi, including *Trichoderma harzianum*[21] and *Myrothecium verrucaria*[22], produce chitinase and chitobiase at appreciable levels. All of these organisms secrete chitinase and chitobiase to the extracellular fluid and thereby provide a route for continuous recovery of the lytic enzyme ensemble. However, enzyme production levels and the efficacy of the enzymes in degrading chitin vary among chitinase-producing bacteria.

EXAMPLE 1

Factorial shake-flask experiments were used to screen a total of 22 microorganisms for chitinolytic activity when grown on a minimal media containing ball-milled crab shell as the only carbon source. Selection of the microorganisms in our screening study was based on earlier studies by Reynolds,[23] Berger and Reynolds,[24] and Monreal and Reese[19] which identified these organisms as exceptionally active on chitin substrates. The shake-flask studies indicated that *Serratia marcescens* is among the most active microorganisms at degrading raw ball-milled chitin. Growth rates for *Serratia marcescens* QM B1466 raised on chitin were at least 30% higher than those for *Enterobacter-liquefaciens*, the microbe showing the next highest chitinolytic activity.

EXAMPLE 2

Media components essential for growth of *S. marcescens* have been determined from a series of 144 factorial shake flask cultures. Optimal compositions for inocula and base-fermentation media, as well as the feed solution, composition for fed-batch fermentations, have then been determined using a $3^f$ factorial design of shake flask cultures in which ball-milled crab-shell chitin serves as the sole carbon source.

Figure 3:
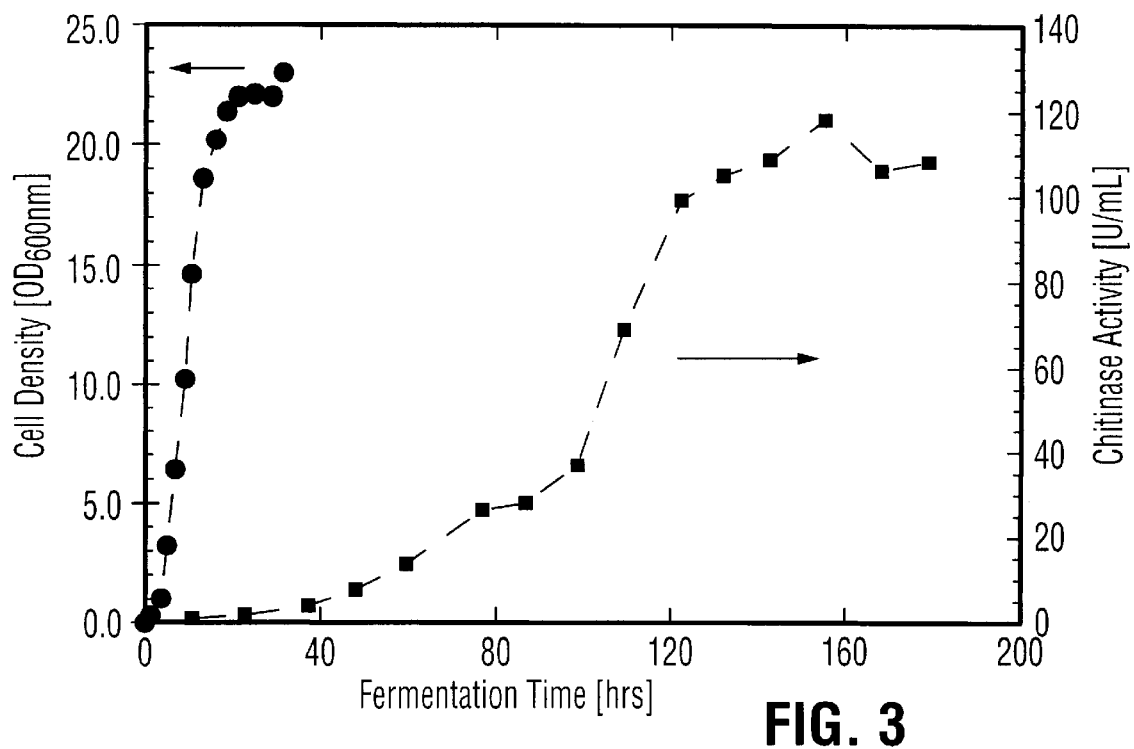
FIG. 3 illustrates a graphical depiction of typical growth and chitinase-activity production curves for the novel optimized fed batch culture protocol according to the invented process.

These optimized media were then applied to the development of a fed-batch fermentation and induction protocol of *S. marcescens* culture. Typical growth and chitinase-activity production curves for the optimized fed-batch culture are shown in FIG. 3. Based on a unit activity of 1 mg N-acetyl-D-glucosamine produced per hour from a colloidal chitin substrate, chitinase activity in the final culture exceeded 105 U/ml, which represents a greater than five-fold increase in volumetric production of the chitinolytic enzyme ensemble over any previous fermentation strategy. In our fed-batch fermentation system, increases in dissolved oxygen, indicating exhaustion of available carbon source in the reactor, are used to control additions of the chitin-containing feed solution to the reactor. The pH and temperature of the reactor may also be controlled for maximum cell growth and chitinolytic enzyme yield.

Chitin or crustacea exoskeleton is periodically added to the fermenter in the form of a sterilized aqueous slurry of pretreated particles of nominal diameter between 50 and 300 $\mu$m. Chitin concentrations in the fermentor have been optimized such that chitin remains the growth limiting nutrient throughout the fermentation which lasts up to six days.

(2) Recovery and Concentration of Chitinolytic-Enzyme Containing Supernatant:

Two chitinases, chitinase A and chitinase B, and chitobiase are the major extracellular enzymes produced when the bacterium *Serratia marcescens* is grown on chitin or chitin-containing crustacea exoskeletons. Together, these enzymes represent over 70% of the total protein content in the supernatant when the four to six day culture induction period is complete. Production of N-acetyl-D-glucosamine does not require further purification of the chitinolytic enzyme ensemble beyond removal of the insoluble cell matter and, in some cases, concentration of the supernatant.

We have developed a number of systems for separating and concentrating the chitinolytic-enzyme containing supernatant from our *S. marcescens* cultures. Binding of chitinase to chitin at 4° C. reaches saturation within 15 minutes and results in a homogeneous colloidal chitin/enzyme slurry containing ca. 7 mg of chitin/enzyme complex per mL, dry weight. Chitobiase also binds chitin at 4° C., but with a much lower affinity. Thus, if necessary, affinity binding to insoluble chitin can be used to partially separate and concentrate chitinase A and B from the supernatant enzyme ensemble.

In the more common case where separation of the chitinolytic enzyme ensemble is not required, we have validated two methods, two-step cross-flow filtration and continuous centrifugation, for separating and concentrating the enzyme solution, both of which are amenable to continuous systems containing solids. Compared to centrifugation, cross-flow filtration is more attractive because of its low cost. We have optimized a two-stage cross-flow filtration system where the (essential) first stage contains a 0.2-$\mu$m filter designed to remove cells and any residual chitin from the supernatant stream, and the (optional) second stage contains an ultrafiltration membrane designed to concentrate the chitinolytic-enzyme ensemble and remove low molecular weight contaminants prior to loading in the chitin-hydrolysis reactor.

(3) Exoskeleton Pretreatment Systems to Improve Enzyme and N-acetyl-D-glucosamine Production:

The results we have obtained indicate that both the rate of chitinolytic enzyme production in the fermenter and the rate of N-acetyl-D-glucosamine production in the chitin hydrolysis reactor are influenced by the properties of the chitin-containing crustacea-shell particles. Of particular importance is the total surface area of chitin per particle available for binding chitinase A and B. The effect of chitin source (eg. crab, shrimp, etc.) has also been investigated and found to influence both chitinase and N-acetyl-D-glucosamine production as well, primarily due to the natural variance in chitin content. Comparison of chitin source indicated that chitinolytic-enzyme production is highest in *S. marcescens* cultures grown on permanganate-washed and cleaned crab shell. Chitinases are also produced in cultures grown on cleaned spot-tail shrimp shells, but are essentially undetectable in oyster-shell, mushroom-chitin, and beetle-chitin containing cultures.

We have explored a number of pretreatment methods including mechanical methods, such as ball milling and hammer milling to increase the external surface area, and physico-chemical methods, such as autoclaving and steam exploding (Parr Bombing™) to swell the crab-shell particles and thereby increase the intraparticle surface area. Treatment with dimethyl-acetimide and weak-acid cosolvents was also explored with the idea of swelling the crab-shell particles through disruption of the interchain hydrogenbond structure.

Figure 16:
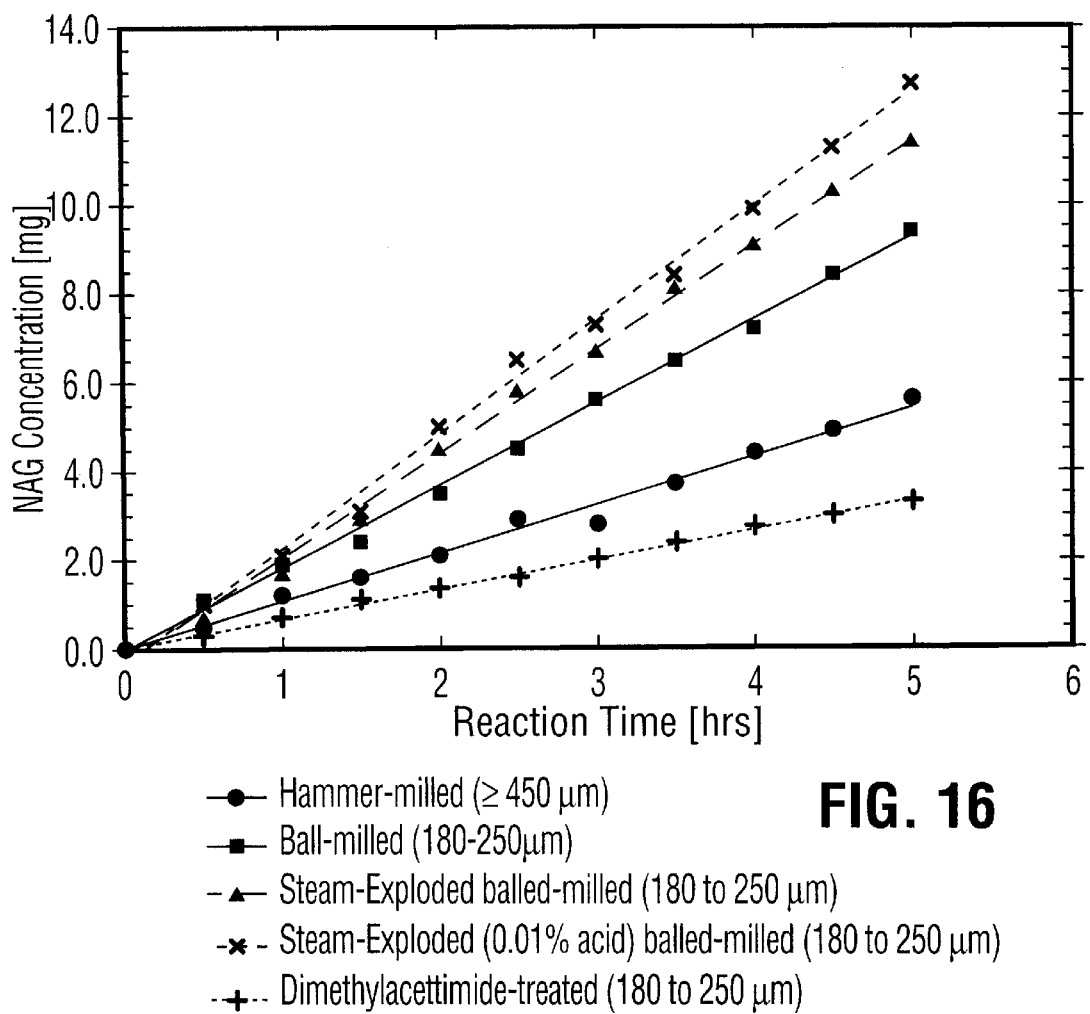
FIG. 16 illustrates a graphical plot of N-acetyl-D-glucosamine (NAG) concentration versus reaction time for chitin which has been hammer-milled, ball-milled, steam-exploded and ball-milled, steam-exploded with acid and ball-milled and treated with dimethyl acetamide.

FIG. 16 illustrates a graphical plot of N-acetyl-D-glucosamine (NAG) concentration versus reaction time for chitin which has been hammer-milled, ball-milled, steam-exploded and ball-milled, steam-exploded with acid and ball-milled and treated with dimethyl acetamide.

EXAMPLE 3

A most promising pretreatment method, as shown in FIG. 16, is steam-explosion of ball-milled chitin containing particles of nominal diameter ranging between 50 $\mu$m and 500 $\mu$m. The steam-explosion gun can be operated over a pressure range of 20 to 2000 psig, a temperature range of ambient to 400° C., and volumetric flowrates up to 20 L s$^{-1}$. Our studies on an aqueous solution containing 20% (w/v) ball-milled shrimp-shell chitin expanded through the steam gun at an inlet pressure of 500 psig and a temperature of 160° C., resulted in an order of magnitude increase in the rate of N-acetyl-D-glucosamine production when 1 mg of treated (vs. untreated) shrimp-shell chitin was contacted with 1 U of chitinase activity for 1 hour at 30° C. and pH 6.5.

EXAMPLE 4

Similar results have been obtained in a batch Parr Bomb™ process where well-stirred chitin-containing particles are incubated with high-pressure steam for between 1 and 2 hours and then blown out a pressure-relief valve to expand the solvent-impregnated particles. Both the steam gun and the Parr Bomb™ technologies were originally designed for treatment of cellulosic materials including wood and, to our knowledge, have never been applied to the treatment of chitin and chitin-containing natural substrates.

A number of chemical pretreatments compatible with the steam gun or Parr Bomb™ including dimethyl acetimide and 0.1% sulfuric acid, have also been investigated. In the chitinase production studies, treatment of ball-milled crab-shell chitin with dimethyl-acetimide and weak-acid cosolvents, which are thought to swell chitin through disruption of the interchain hydrogen-bond structure, resulted in small (2% to 5%) increases in chitinase activity.

(4) Two-Stage Bioreactor for the Production of N-acetyl-D-glucosamine by Enzymatic Hydrolysis of Chitin-containinq Solids:

The design of the described invented reactor is based on a series of fundamental data collected in the laboratory which determine: (1) the solution conditions where the chitinolytic-enzyme ensemble shows maximum activity, (2) the effects of chitin source and pretreatment on N-acetyl-D-glucosamine production rates, (3) the stability of the enzyme-ensemble as a function of solution pH and temperature, and (4) the existence, degree and mechanism of enzyme inhibition caused by one or more of the hydrolysis products. We have addressed each of these issues and used the results as a basis for design of a novel effective chitin-hydrolysis bioreactor.

EXAMPLE 5

Maximum hydrolytic activity of the chitinolytic-enzyme ensemble recovered from supernatants of *S. marcescens* cultures was found between pH 6 and 7 from 45° C. to 49° C.

As detailed in Examples 3 and 4, steam explosion of shrimp-shell or crab-shell particles milled to a nominal diameter between 50 $\mu$m and 500 $\mu$m yields maximum N-acetyl-D-glucosamine production rates among the various chitin sources and pretreatment methods explored. However, the process can be applied to all chitin-containing substrates in any form at any level of pretreatment.

Half-lives of chitinase and chitobiase activity in chitinolytic-enzyme ensemble solutions recovered from *S. marcescens* cultures are 3.8 days and 2.7 days, respectively, at 40° C. and pH 6.5; the half-lives drop to 2.6 days and 1.7 days when the temperature is raised to 45° C.

Total chitinase and chitobiase activities are noncompetitively inhibited to an extreme of 30% maximum activity by the desired hydrolysis product N-acetyl-D-glucosamine.

These results indicate that chitin hydrolysis rates will be highest in a reactor maintained near pH 6.5 and 40° C. which controls the concentration of N-acetyl-D-glucosamine in the reactor such that it is maximized at the outlet of the reactor but remains at sub-inhibitory levels in (at least much of) the remainder of the reactor. Two reactor configurations meet these criteria: (1) a packed-bed reactor, where the mobile phase carries the chitinolytic enzyme ensemble and the hydrolysis products through a packed bed of chitin containing solid particles, and (2) a fluidized-bed reactor where the upward velocity of the mobile phase partially or fully suspends the chitin-containing particles in the flow field.

The packed-bed reactor, two configurations of which are shown in FIGS. 2a and 2b, offers the advantages that the concentration of chitin in the reactor is maximized and the flow profile and flow rates through the bed can be adjusted to maximize chitin hydrolysis rates.

Figure 2C:
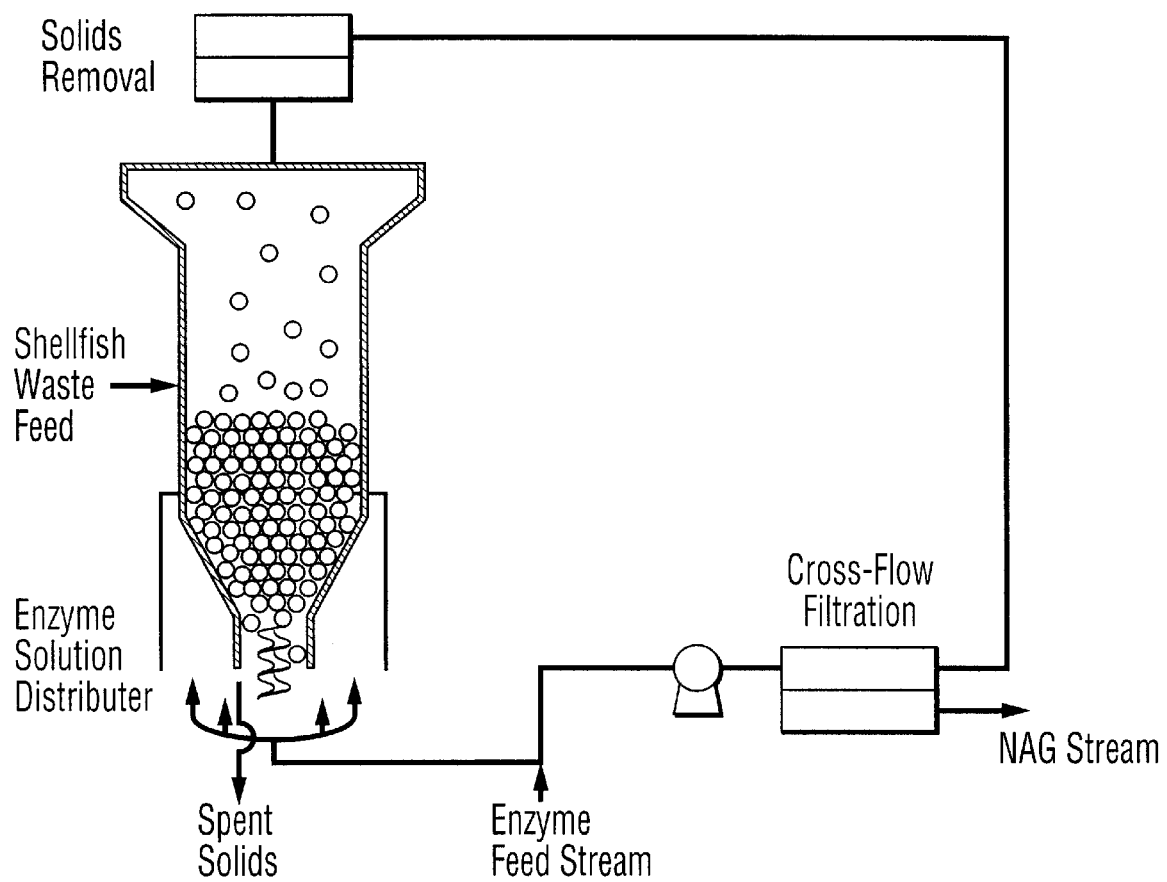
FIG. 2c illustrates a schematic depiction of a semi-fluidized bed chitin-hydrolysis bioreactor.

The fluidized-bed reactor illustrated in FIG. 2c increases the available chitin surface area per particle and lowers pumping requirements, by diminishing the pressure drop across the bed, at the expense of increasing end-product inhibition effects in the reactor.

EXAMPLE 6

The two-stage chitin-hydrolysis bioreactor according to the invention maintains high rates of chitin hydrolysis and provides N-acetyl-D-glucosamine as the only substantial final reactor product. Two possible configurations of the invented bioreactor are shown in FIGS. 2a and 2b. Focusing the illustrative discussion on the configuration shown in FIG. 2a, we have designed a novel reactor for N-acetyl-D-glucosamine where the bottom ca. two-thirds of the working volume of the reactor is a packed bed of chitin containing particles. The mobile phase containing the chitinolytic enzyme ensemble passes upward through the bed. When the enzyme ensemble comes into contact with the chitin, the chitinases adsorb and catalyze the hydrolysis reaction; N-acetyl-D-glucosamine and soluble oligosaccharides are released and accumulate with increasing distance travelled up through the packed bed. This concentrated mixture of N-acetyl-D-glucosamine and soluble oligosaccharides then enters the upper ca. 1/3 of the reactor, which contains no insoluble chitin and is relatively enriched in chitobiase since it is the only member of the chitinolytic enzyme ensemble which does not adsorb to chitin. The volume of and liquid residence time in this insoluble-chitin-free portion of the reactor are set such that all of the soluble oligosaccharide which exits the packed-bed portion of the reactor is completely hydrolyzed to N-acetyl-D-glucosamine, making N-acetyl-D-glucosamine the only sugar product of the two-stage reactor.

The enzyme feed solution enters the bottom of the packed bed where substrate concentrations are highest and N-acetyl-D-glucosamine concentrations are at a minimum. Thus, as with any packed-bed reactor, N-acetyl-D-glucosamine production rates are maximized near the column inlet and steadily decrease with increasing upward distance through the column which corresponds to increasing N-acetyl-D-glucosamine concentration in the column. The reactor is maintained at pH 6.5 and an isothermal reactor temperature between 35° C. and 50° C. Action of the enzyme feed solution on ball-milled chitin appears to yield only N-acetyl-D-glucosamine and no appreciable amounts of higher chito-oligomers in the product stream.

The enzyme catalyst stream is continuously recycled to the reactor inlet after removing the N-acetyl-D-glucosamine product by continuous cross-flow filtration across a 10 kD MW cutoff membrane. Additional enzyme is added to the feed stream to compensate for enzyme deactivation with time. Pretreated crustacea shell particles are added to the top of the bed either continuously or semicontinuously to maintain an optimum chitin concentration in the reactor.

(5) Final Purification of N-acetyl-D-glucosamine and Chitinolytic Enzyme Ensemble:

A continuous cross-flow ultrafiltration system is used to separate the N-acetyl-D-glucosamine product from the chitinolytic-enzyme ensemble. The enzyme ensemble is retained by the filter and can either be recycled to the bioreactor or recovered. The N-acetyl-D-glucosamine product in the filtrate stream has a purity greater than 98% (w/v). No protein contaminants are detactable. The primary oligosaccharide contaminant is chitobiose. A variety of precipitating agents, including ammonium sulfate, can be used to recover a semi-crystalline N-acetyl-D-glucosamine powder from the filtrate solution.

Verification of N-acetyl-D-glucosamine Production

The process of the invention is currently capable of producing N-acetyl-D-glucosamine at an average rate of 78 ($\pm$7) g $L^{-1}$ $hr^{-1}$ in the configuration shown in FIG. 1a with a two-stage reactor of the type shown in FIG. 2a. The fermentation is carried out between pH 7 and 8 at 30° C., producing 101 ($\pm$6) U/mL of chitinase activity. The chitinolytic enzyme ensemble is then purified by a continuous two-stage membrane filtration and diluted tenfold to a bioreactor feed concentration of 10 U/mL chitinase activity. The two-stage bioreactor has been operated continuously over a ten day period, reaching steady-state production levels after 28 hours, and producing a greater than 98% purity N-acetyl-D-glucosamine product from that time until the process was terminated.

Figure 4:
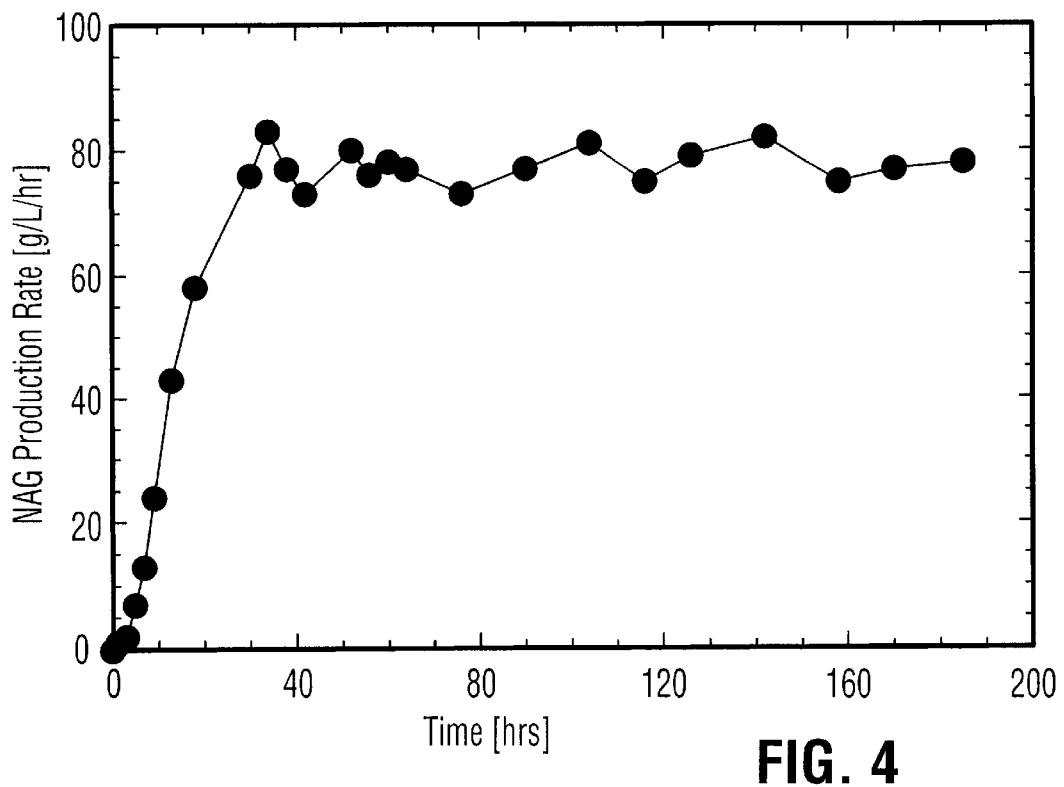
FIG. 4 illustrates a graphical depiction of measured N-acetyl-D-glucosamine production rates as a function of operation time for the process of the invention as measured by high-performance liquid chromatography assays of the process stream leaving the top of the two-stage reactor.
Figure 5:
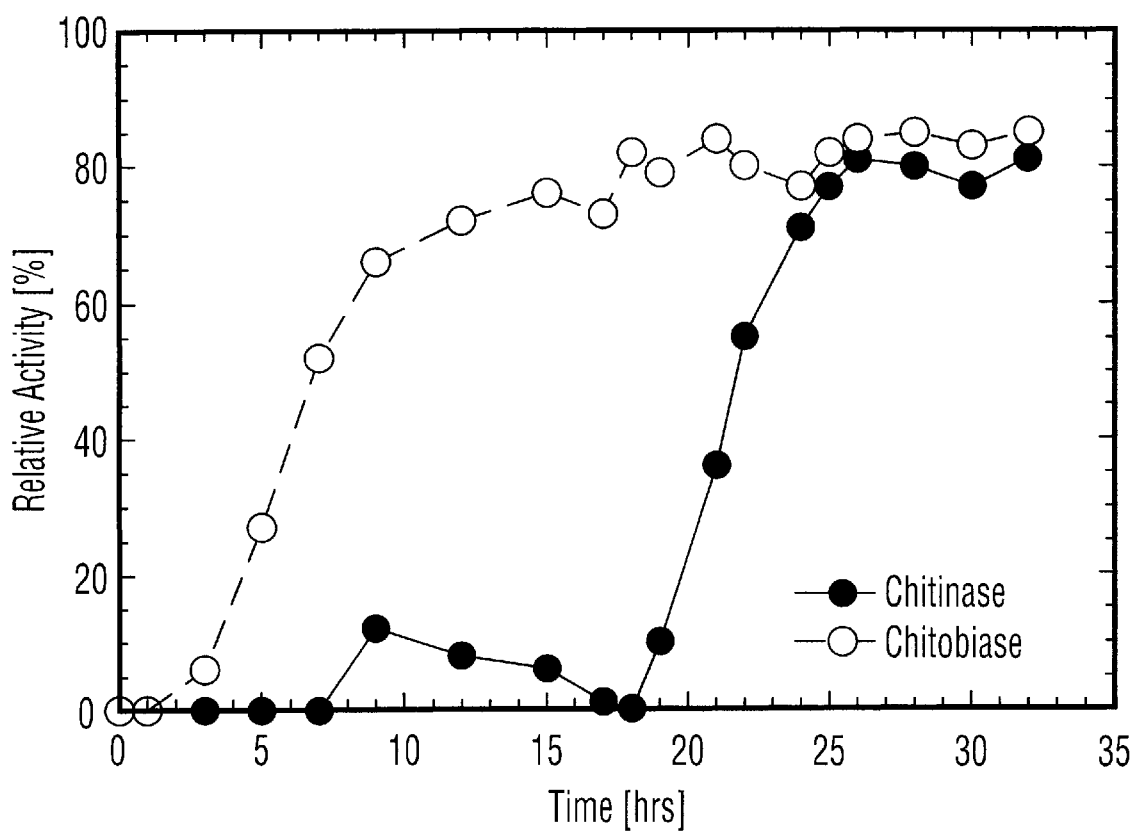
FIG. 5 illustrates a graphical depiction of measured activities, relative to that measured for 10 U/mL chitinolytic-enzyme-ensemble mobile phase which was initially introduced into the reactor, for the chitinase enzymes and for chitobiase in the process stream leaving the top of the two-stage reactor as a function of operation time.
Figure 6B:
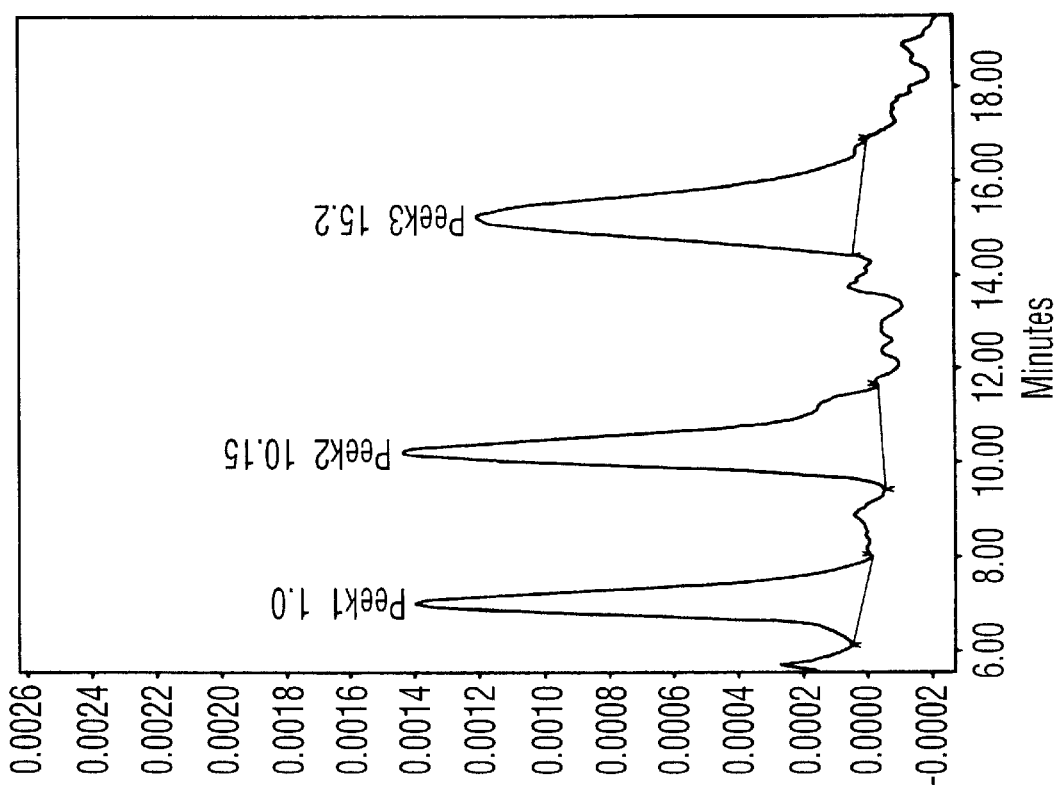
FIGS. 6a and 6b compare a chromatogram of the N-acetyl-D-glucosamine product recovered from the filtrate stream of the final cross-flow filtration with a standard solution containing N-acetyl-D-glucosamine, chitobiose and chitotriose.
Figure 6A:
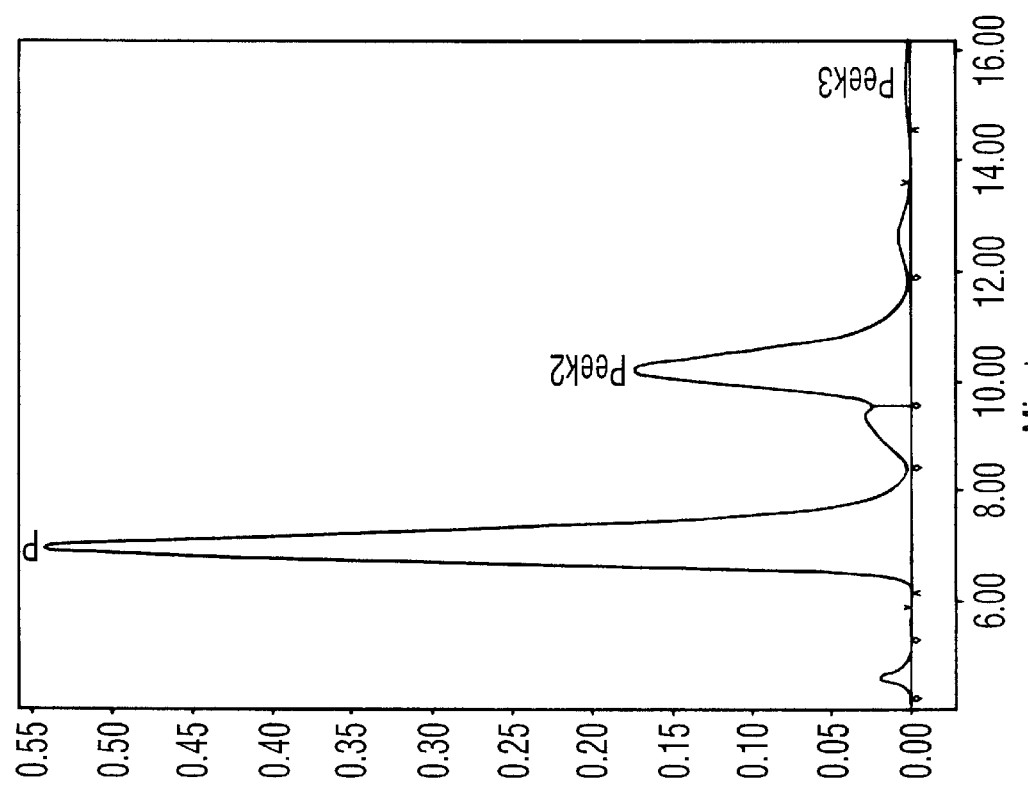

FIG. 4 shownss measured N-acetyl-D-glucosamine production rates as a function of operation time for the process of the invention as measured by high-performance liquid chromatography assays of the process stream leaving the top of the two-stage reactor. FIG. 5 shows measured activities, relative to that measured for 10 U/mL chitinolytic-enzyme-ensemble mobile phase which was initially introduced into the reactor, for the chitinase enzymes and for chitobiase in the process stream leaving the top of the two-stage reactor as a function of operation time. The initial absence of chitobiase activity in the reactor outlet stream is consistent with the void volume of the reactor. The absence of chitinase activity in the reactor outlet stream provides evidence that chitinase enzymes adsorb to the chitin in the packed bed of ball-milled shrimp shell particles. After 28 hours of continuous operation, the shrimp shells become saturated with adsorbed chitinase enzymes and a steady-state level of chitinase activity is recorded in the reactor outlet stream. FIG. 6 compares a chromatogram of the N-acetyl-D-glucosamine product recovered from the filtrate stream of the final cross-flow filtration with a standard solution containing N-acetyl-D-glucosamine, chitobiose, chitotriose, and chitotetraose. N-acetyl-D-glucosamine is the only detectable product from the process of the invention.

EXAMPLE 7

Laboratory Materials and Methods

Practical-grade crab-shell chitin was obtained from Sigma Chemicals Inc. (St. Louis, Mo.). Shrimp and oyster shells were obtained from local shellfish processing plants (get ref.). All salts and solvents were purchased from BDH Chemicals Inc.

*Serratia marcescens* QM B1466 Cultures

Streak cultures of *S. marcescens* QM B1466 were maintained on nutrient agar (0.8% nutrient broth, 1.5% agar) (Difco Laboratories, Detroit, Mich.) at 4° C. and transferred every 2 weeks. Original plates were prepared by streaking from glycerol stock (stored at −70° C.) and incubating at 30° C. for 24 hours.

25-mL inoculum cultures of *S. marcescens* contained YEPD medium at concentrations of 1 wt % yeast extract (Difco), 2 wt % peptone (Difco), and 2 wt % glucose (BDH inc., Toronto, Canada). A first inoculum culture was grown overnight at 30° C. and pH 7.0 and used to inoculate a second identical culture. This culture was grown at identical conditions for 3 hours, at which time the culture was in full exponential growth.

Batch shake-flask culture experiments were performed in 125-mL shake flasks containing 15 g/L practical grade crab-shell chitin, 0.5 g/L yeast extract (Difco), 1.0 g/L $(NH_4)_2SO_4$, 0.3 g/L $MgSO_4$, and 1.36 g/L $KH_2PO_4$ (Monreal and Reese, 1969). The pH of the medium was adjusted to 8.5 width 1.0-M NaOH before steam sterilization. All shake-flask cultures were inoculated (1%) with the second (3 hour) inoculum culture.

Substrate Preparation

Washed crab, shrimp and oyster shells (containing chitin) were processed in one or more of the following ways: (1) ball-milling, (2) autoclaving of a 2% chitin suspension in either distilled water, 1% (v/v) sulfuric acid, or 1% (v/v) N,N-dimethyl-acetamide (DMA), a reported solvent for chitin (Austin, 1988), and (3) steam-explosion of a 2% chitin suspension in either distilled water or 1% (v/v) DMA.

Crustaceal exoskeletons were ball-milled for 3 hours in a Morton three-tier jar mill containing thirty 2-cm diameter burundum balls per 50 grams of crab shell. Ball-milled crab-shell particles ranged in size from ca. 40 $\mu$m < nominal diameter <400 $\mu$m and were sieved on a shaker assembly to obtain five size fractions, each covering about an 80 $\mu$m nominal particle diameter range. Ball-milling of both shrimp and oyster shells resulted in a fine powder of less than 50 $\mu$m nominal diameter and no further size fractionation was performed.

Autoclaving of sieved crab-shell chitin solutions was performed for 20 minutes in a Market Forge Sterilmate operating at a steam temperature of 121° C. Steam explosion of sieved crab-shell chitin was performed in a 316 stainless steel Parr™ model 4522 2-L reactor (Parr Instrument Co., Moline Ill.). Chitin slurries were heated to a desired temperature (either 190 or 225° C.) and the resulting steam pressure, held there for 10 minutes, and then rapidly expanded to atmospheric pressure through a ball-type discharge valve. Autoclaved and steam-exploded chitin samples were centrifuged and twice washed with excess volumes of distilled water before being used in batch culture experiments.

Swollen chitin was prepared according to the method of Berger and Reynolds, 1958. Ball-milled crab and shrimp shells were first soaked in 2 wt % $KMnO_4$ solution at room temperature for 15 to 20 hours to remove pigments. The remaining powder was then washed with a 1 wt % oxalic acid solution to reduce the residual $KMnO_4$ and $MnO_2$.

Swollen colloidal chitin (used primarily as a reference for enzymatic assays) was prepared by washing swollen chitin with acetone to form a chitin paste, then slowly adding the paste to 7 to 9 volumes of concentrated HCl cooled in an ice bath to 4° C. to arrest hydrolysis. Particulates were removed from the syrupy liquid by filtering in a glass column containing a sintered glass plate and loosely-packed glass wool. The decalcified chitin filtrate was dropped into a vigorously stirred aqueous 50% ethanol solution to precipitate the chitin in a highly dispersed state. The colloidal residue was centrifuged at 5000×g for 20 minutes and resuspended in water three to five times, then sedimented by gravity and washed several times with a 100-mM potassium phosphate buffer containing 1-mM $CaCl_2$ (pH 6.0) to rmeove excess acid and alcohol. Finally, the swollen chitin solution was dialyzed against 100-mM potassium phosphate buffer until a pH of 5 to 6 was maintained.

Fermentations

Batch fermentations were performed in a 10-L Chemap fermentor with the temperature controlled at 30° C. Fermentations were performed using a 7-L working volume and the same media as used in shake-flask experiments (15 g/L practical grade crab-shell chitin (Sigma), 0.5 g/L yeast extract (Difco), 1.0 g/L $(NH_4)_2SO_4$, 0.3 g/L $MgSO_4$, and 1.36 g/L $KH_2PO_4$ (All BDH)), pH 8.5. The fermentor was inoculated (5%) with 3-hour YEPD inoculum culture as described for batch cultures.

A fed-batch fermentation was also performed using a 10-L working volume. The temperature and pH were controlled at 30° C. and 7.0, respectively. Glucose was used as the carbon source until high cell density was achieved, at which time the carbon source was switched to ball-milled practical grade crab chitin. Minimal media was used for both the inoculum and the fed-batch fermentation media; the composition, based on studies by Veron, 1975, is given in Table 1. During the glucose-feeding portion of the fermentation, glucose levels were monitored at regular intervals using a Beckman Glucose Analyzer 2.

Chitinase Activity Assays

Total chitinase activity was measured by the calorimetric method of Reissig et al., 1955, with some modifications to allow for multi-sample analysis using an ELISA 96-well plate reader. The reaction mixture contained 0.8 mL of a 0.125% (w/v) suspension of swollen colloidal chitin and 0.1 mL of 100-mM potassium phosphate buffer (containing 1.0-mM $CaCl_2$) at pH 6.0. The reaction mixture was mixed with 0.1 mL of enzyme (culture supernatant) solution diluted 5 to 200 fold in the same phosphate buffer and incubated at 37° C. for 1 hour, at which time the reaction was quenched by boiling for 5 minutes. A chitin blank and each sample were then centrifuged at 5000×g for 5 minutes and 0.275 mL of each supernatant was collected and assayed for NAG concentration.

N-acetyl-D-glucosamine (NAG) concentrations were determined by mixing 0.055 mL of 0.8-M potassium tetraborate (pH 9.1) with the 0.275-mL supernatant sample and heating the resulting solution in a vigorously boiling water bath for 3 minutes. The mixture was then cooled immediately in an ice bath. 100 mL of the mixture was deposited, in triplicate, in ELISA plate wells; NAG-standard and blank solutions were also added to the plate in triplicate. 100 mL of 0.112-M p-dimethylamino-benzaldehyde (Ehrlich's reagent) in analytical-grade glacial acetic acid (containing 12.5% w/v) 10-N HCl) was then added to each well and the plate was maintained at 37° C. for precisely 20 minutes. The plates were cooled to 4° C. for 3 minutes and the absorbance of each well was subsequently measured at 545 nm in an ELISA plate reader. One unit of activity was defined as the amount of enzyme able to liberate 1 mg of N-acetyl-D-glucosamine per hour.

Chitinase activity was also determined by using the analog p-nitrophenyl-β-D-N,N'-diacetylchitobiose (pNP-(NAG)$_2$) (Sigma). The assay was performed in triplicate using ELISA plates and contained 50 μL of 100 mM KH$_2$PO$_4$ buffer containing 1-mM CaCl$_2$ at pH 6.0, 50 μL of pNP(NAG)$_2$ dissolved in nanopure water (400 μg/ml) and 20 μL of enzyme diluted in the same buffer. After 10 minutes of incubation samples were read at 405 nm using an ELISA plate reader. Blanks were used to discount any absorption due to the enzyme or pNP-(NAG)$_2$ alone. The μmoles of p-nitrophenol released by the samples was calculated using a standard curve. Units of enzymatic activity were determined as the number of μmoles of p-nitrophenol released per minute under the assay conditions.

Chitobiase Activity Assay

Chitobiase activity was determined by measuring the amount of p-nitrophenol released when an aliquot of enzyme solution (culture supernatant) was incubated with an aqueous solution of p-nitrophenyl-N-acetyl-β-D-glucosamine (pNP-NAG) (Sigma). The buffer used in this assay was 85-mM Tris(hydroxymethylaminomethane)-malate, pH 7.0. 50 μL of 2.5-mM pNP-NAG solution was mixed with 50 μL buffer and 20 μL of enzyme solution appropriately diluted in buffer. After a 10-minute incubation period at 37° C., the reaction was stopped by the addition of a 100 μL of 0.375-M Na$_2$CO$_3$ (Yabuki et al., 1986). The liberated p-nitrophenol was spectrophotometrically measured at 405 nm in an ELISA plate reader. One unit of chitobiase activity is equal to the amount of enzyme necessary to liberate 1 μmol of p-nitrophenol per minute.

Analysis of Chitin-Hydrolysis Products

Chitinase action on swollen colloidal chitin was analyzed by HPLC using a Radial-Pak μBondapak-NH$_2$ column (8×100 mm, Waters) as described in Ohtakara and Mitsutomi, 1988. N-acetyl-D-glucosamine and chitooligomer retention times were identified by running standards (YSK Ind. Co., Ltd., Tokyo, Japan). Peaks were detected at 210 nm.

Results and Discussion

Optimization of Culture Conditions

Economical production of N-acetyl-D-glucosamine requires optimization of media composition (and culture conditions) such that chitinolytic enzyme production is maximized at a minimum media and operating cost. Optimized media for batch cultures of *S. marcescens* was based on refinement of the recipe of Monreal and Reese, 1969 (see Table 1) using results from factorial shake-flask experiments designed to maintain chitin as the growth limiting nutrient throughout the culture. The concentrations of yeast extract, (NH$_4$)$_2$SO$_4$, MgSO$_4$, and KH$_2$PO$_4$ were all allowed to vary while holding ball-milled crab-shell chitin content constant at 15 g/L. Table 1 showns the resulting media optimized for minimum media cost. At concentrations above those in the optimized media reported in Table 1 below, the media composition has little effect on chitinase production or cell density after 160 hours of culture.

Fermentations

Figure 7A:
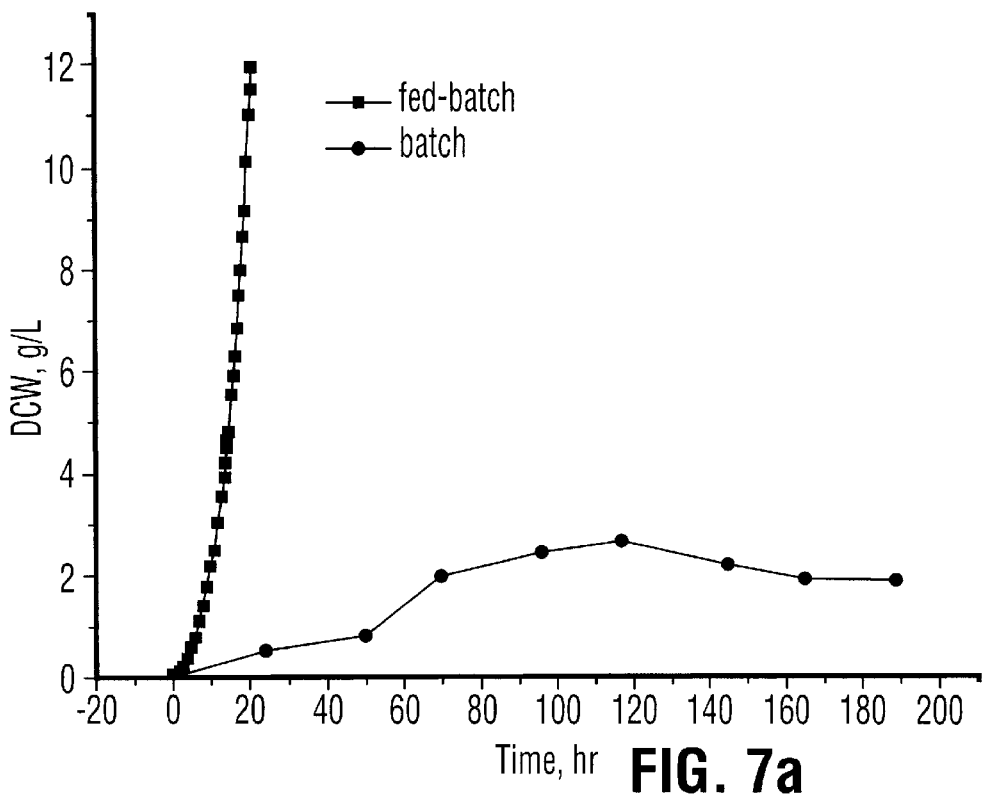
FIG. 7a illustrates growth curves for *Serratia marcescens* 10-L fed-batch (minimal media) grown on glucose and 7-L batch fermentations at 30° C.

FIG. 7a shows dry cell weights (DCW) as a function of time for a typical 7-L batch fermentation grown for 8 days. This figure also shows data for a 10-L fed-batch fermentation of *S. marcescens* QM B1466 grown for 20 hours on the defined minimal media shown in Table 1 (where glucose is the sole carbon source), after which time ball-milled crab-shell chitin was added to a final concentration of 1.5% (w/v) to test chitinase induction at high cell densities. All glucose in the fermentor was exhausted prior to addition of the chitin substrate in order to minimize, but not necessarily eliminate, glucose repression. The final OD$_{660nm}$ of ca. 22 prior to chitin addition in the fed-batch culture represents a substantial increase in cell density over conventional batch cultures of *S. marcescens* grown on either glucose or chitin (maximum OD$_{660nm}$ of 3). Thus, we could realize a substantial increase in volumetric yield of chitinase activity provided equivalent production of chitinase activity per cell could be achieved.

Figure 7B:
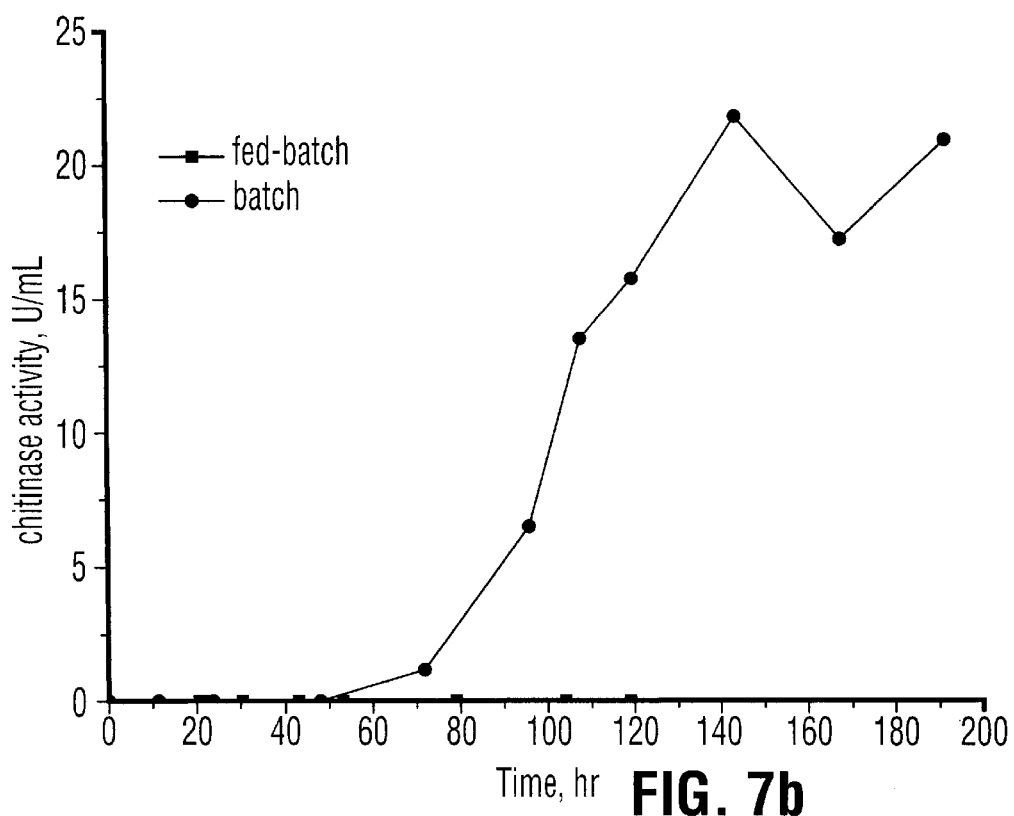
FIG. 7b illustrates chitinase production for a batch fermentation using chitin as the sole carbon source and for a fed-batch (10-L) fermentation using glucose as the initial carbon source and inducing with chitin at early-stationary phase growth, 30° C.

FIG. 7b shows chitinase-activity as a function of culture time for each of the above fermentations. Chitinase activity is not observed in the batch fermentation until late in the second day, after which it steadily rises until a maximum activity between 20 and 25 U/mL is reached near 140 hours of culture. Culture times, as well as intermediate and final chitinase activities, are very similar to those observed in the optimized shake-flask cultures, indicating that mass-transfer limitations due to the insoluble nature of the chitin substrate are not exacerbated by scale-up.

Chitinase-activity is never observed in the high-cell-density fed-batch culture, where the cells were induced with 1.5% (w/v) chitin during late exponential phase growth. One possible explanation for the absence of chitinase production in this system is that the cells in this late growth stage are stressed to the point where they can no longer accept chitin as a carbon source. Batch cultures grown on glucose to early exponential-phase growth and a wide range of cell densities were induced by exhausting the glucose, and immediately exposing the culture to 1.5% (w/v) ball-milled crab-shell chitin. In each case, an increase in cell density of 4 to 5 OD$_{660nm}$ was observed over a five day growth period. The resulting chitinase activity as a function of induction time was, within experimental error, identical to that observed for the low-cell-density batch culture grown exclusively on chitin. This suggests that chitinolytic activity was only produced in that small fraction of cells which grew on chitin, while the bulk of the culture remained glucose repressed.

Chitin Source and Pretreatment

Since the economics of the process of the invention will be largely defined by the cost of producing the chitinolytic enzyme ensemble, we have explored the effects of chitin source, as well as a number of inexpensive methods for preparing the chitin substrate, on *S. marcesces* growth and chitinase production.

Figure 8A:
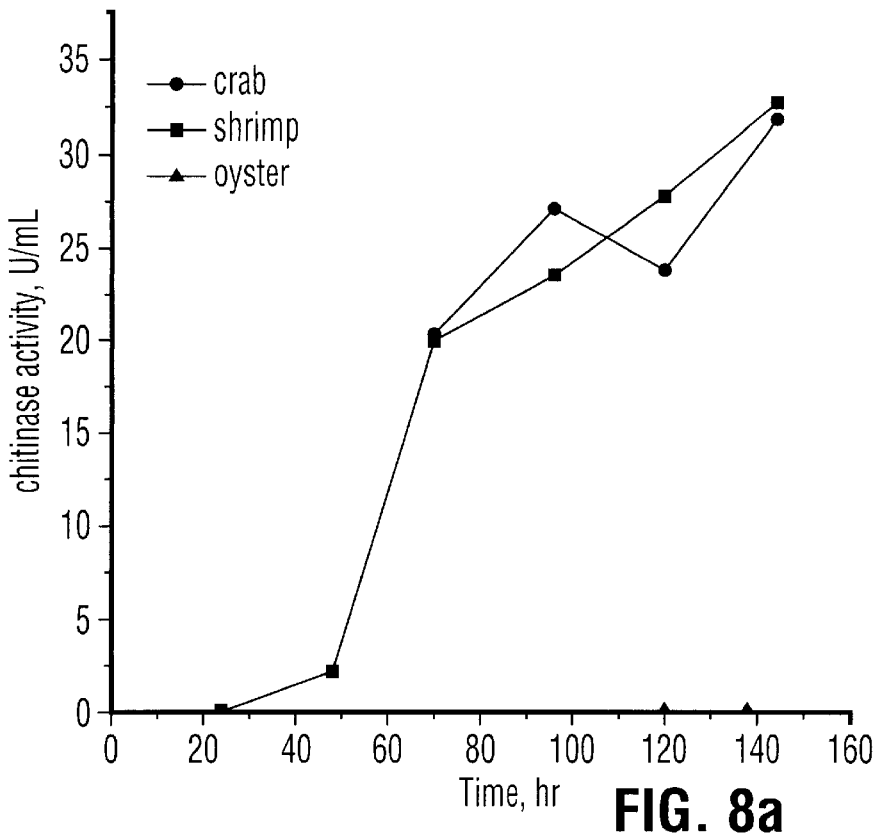
FIG. 8a illustrates the effect of chitin source on chitinase production in *S. marcescens* batch culture, 30° C.
Figure 8B:
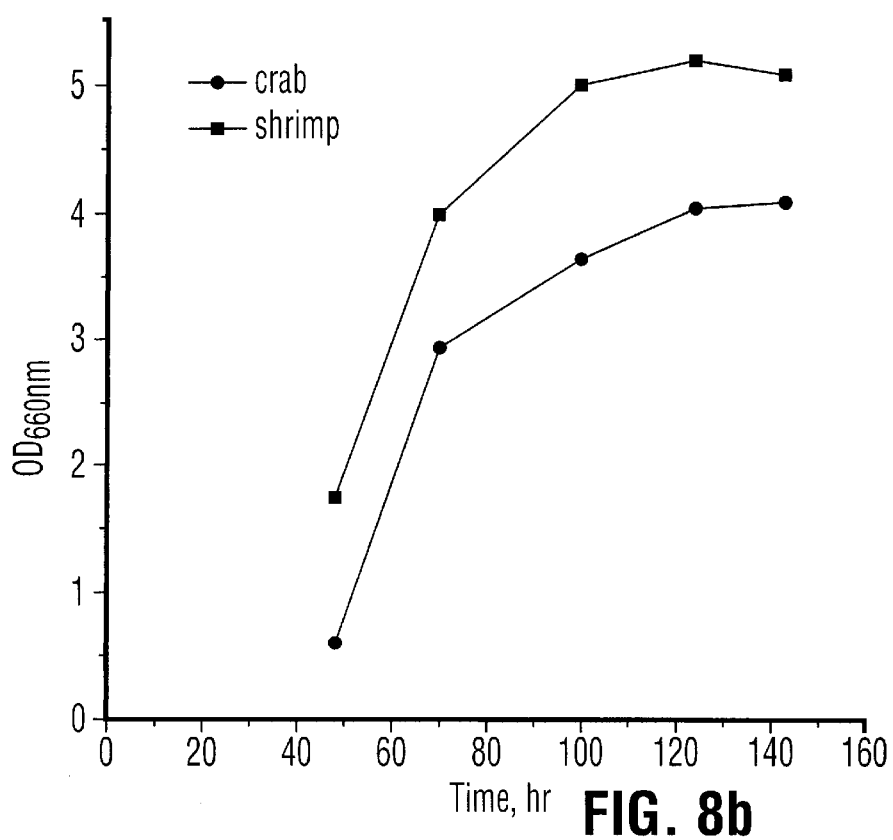
FIG. 8b illustrates cell growth in batch culture of *S. marcescens* grown on crab and shrimp chitin, 30° C.

FIG. 8a shows the influence of chitin source on the production of chitinolytic enzymes and cell growth in otherwise identical shake-flask cultures of *S. marcescens* QM B1466. In each of these cultures, equivalent concentrations of chitin were supplied as a ball-milled exoskeleton powder of similar particle size. As shown in FIG. 8a, chitinolytic enzyme production is similar for S. marcescens cultures grown on crab and shrimp chitin, but is essentially undetectable in the oyster-shell culture, indicating relatively poor presentation of chitin in this latter system. Similar cell growth and final cell densities were observed for growth on equivalent concentrations of crab and shrimp shells (FIG. 8b). In both systems, free N-acetyl-D-glucosamine concentration remained low while the cell population was increasing. Little to no cell growth was observed in the cultures grown an oyster shells.

Since chitinases can only hydrolyze solvent-accessible β-1,4-linkages, the effective surface area and morphology of crab-shell waste may influence both enzyme production and catalytic activity. We have explored a number of inexpensive substrate pretreatments aimed at increasing chitinase activity in culture supernatant. These include ball milling to increase the external surface area to volume ratio of the particles, and both autoclaving and the more severe steam-explosion technique to swell the crab-shell particles and thereby (possibly) change chitin availability and morphology. Autoclaving was done both in distilled water and in dilute solutions of either dimethyl-acetamide or sulfuric acid to swell the crab-shell particles through disruption of the interchain hydrogen-bond structure. Dimethyl-acetamide was chosen because it has been shown to be an effective solvent for chitin (Austin, 1988); sulfuric acid is commonly used as a swelling agent in the treatment of cellulose (Mackie et al., 1985). FIG. 16 illustrates a graphical plot of N-acetyl-D-glucosamine (NAG) concentration versus reaction time for chitin which has been hammer-milled, ball-milled, steam-exploded and ball-milled, steam-exploded with acid and ball-milled and treated with dimethyl acetamide.

Figure 9A:
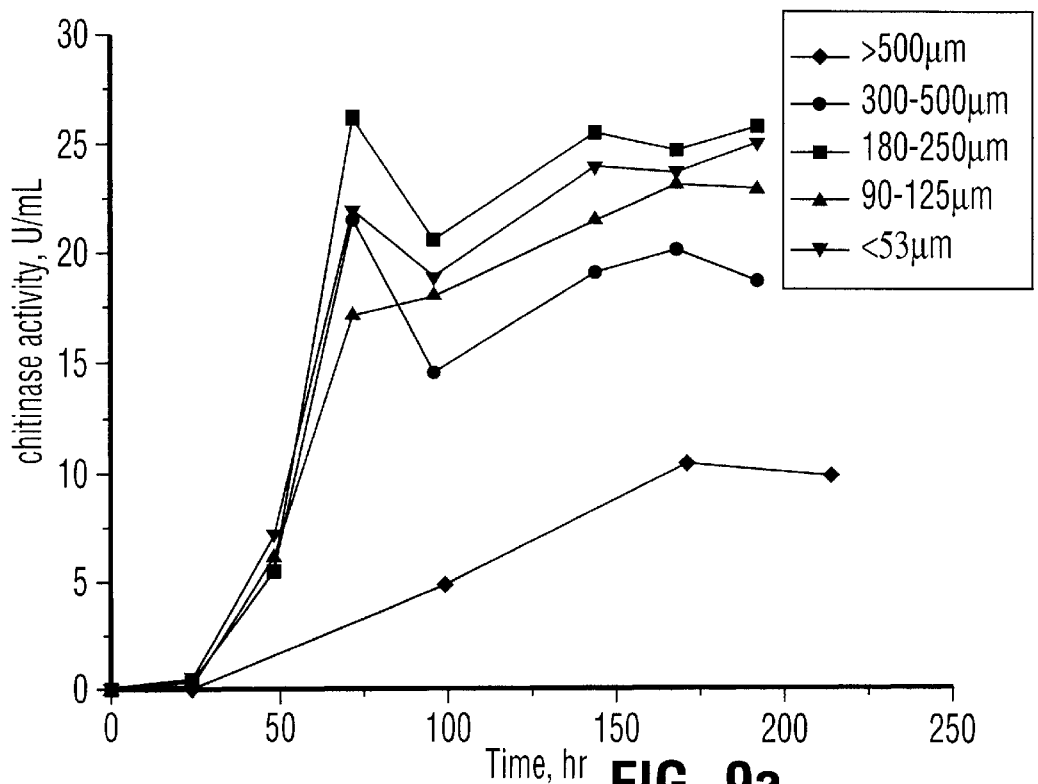
FIG. 9a illustrates the effect of chitin particle size on chitinase production, batch culture 1.5% chitin, 30° C.

FIG. 9a shows the effect of nominal particle diameter $D_n$ on the production of chitinase activity in shake-flask cultures of S. marcescens. Final chitinase activity slightly more than doubles when $D_n$ is decreased from ca. 600 $\mu$m to 400 $\mu$m, which is directly proportional with the 2.25-fold increase in average surface area per unit particle. However, no significant increase in maximum chitinolytic activity is observed when the particle diameter falls below 180 $\mu$m. Final cell densities were similar in all cultures (maximum $OD_{660nm}$ of 3).

Figure 9B:
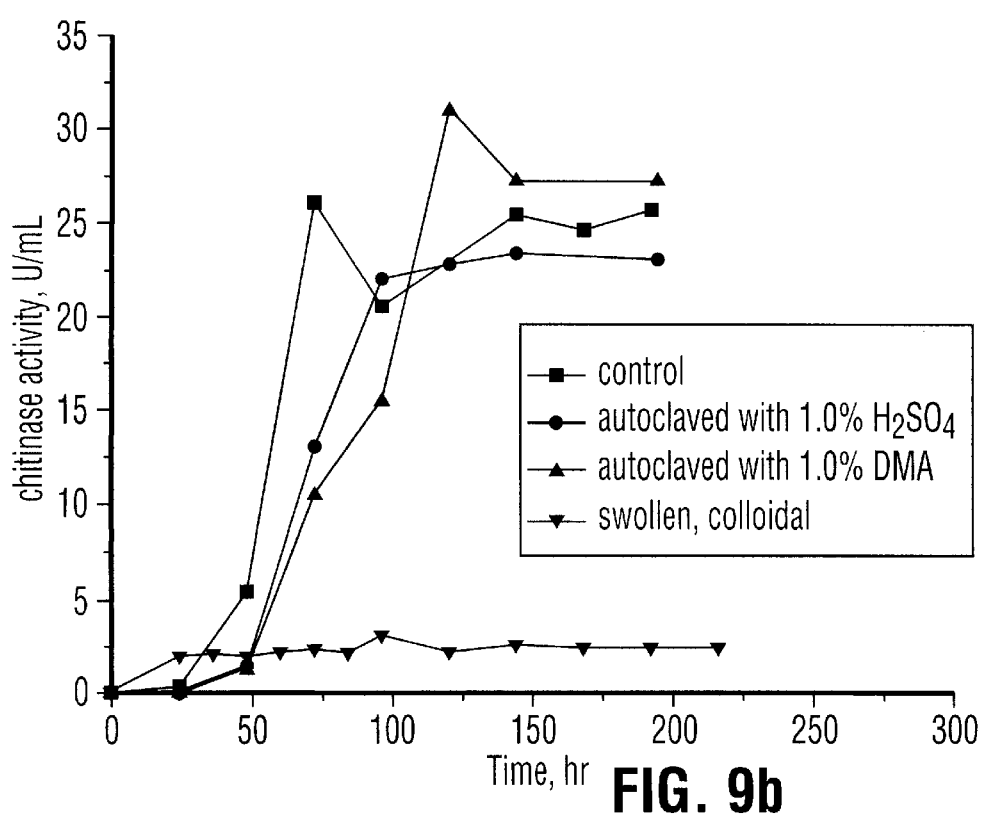
FIG. 9b illustrates the effect of crab-shell chitin pretreatment on chitinase production in batch culture, 1.5% chitin, 30° C., 300 µm particle size (except colloidal chitin).
Figure 9:
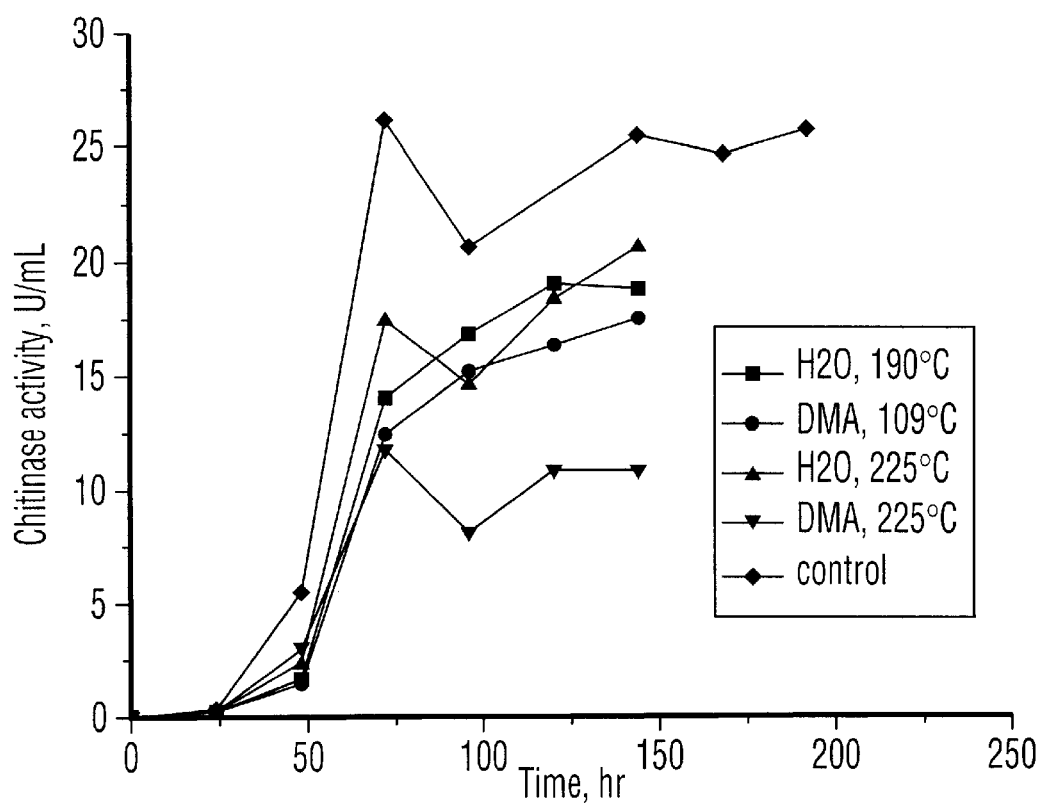
FIG. 9c illustrates the effect of steam explosion pretreatment on chitinase production.

As shown in FIG. 9b, autoclaving (at 121° C.) of the 180 $\mu$m to 250 $\mu$m sieved fraction in 1% DMA results in a small but reproducible increase in chitinase activity, indicating that a change in particle morphology can lead to higher yields. However, no improvement was observed when the solvent was either distilled water (not shown) or 1% $H_2SO_4$. Moreover, as shown in FIG. 9c, the more aggessive steam-explosion pretreatment of the same particle size fraction results in a substantial reduction in chitinase production with increasing severity of processing conditions. Maximum chitinase activity is reduced by more than a factor of 2 for crab-shell samples in 1% DMA steam exploded at 225° C., and by more than a factor of 6 for swollen colloidal chitin, where all non-chitinaceous contaminants have been removed. Viewed together, FIGS. 9a, 9b and 9c indicate that chitinase production has a strong nonlinear concave-down dependence on chitin/NAG availability in the crustacea-shell substrate. At low available chitin concentrations, chitinolytic enzyme production increases with increasing chitin/NAG availability. Harsher pretreatment of crab-shell particles, designed to increase chitin availability per gram of substrate, results in an increase in (initial) free NAG concentration in the culture which is quickly exhausted by the expanding cells. No chitinolytic activity is produced in S. marcescens cultures grown on NAG. The repression of chitinolytic enzyme production observed under these conditions may therefore be due to an excess of free NAG combined with abundance of available chitin, including soluble chitin oligomers.

Rate-limitinq Step in N-Acetyl-D-Glucosamine Production

Figure 10:
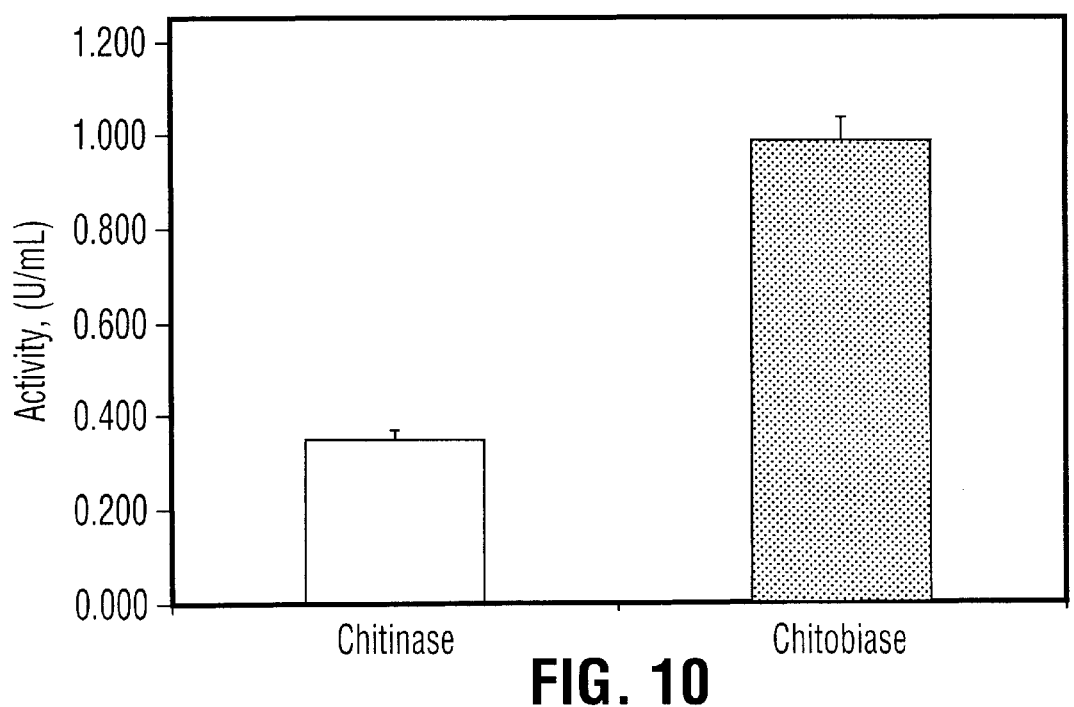
FIG. 10 illustrates relative chitinase (open bar) and chitobiase (shaded bar) activities in crude extracts from S. marcescetis cultures which were determined using p-nitrophenyl-β-D-N,N'-diacetylchitobioseandp-nitrophenyl N-acetyl-β-D-glucosaminide respectively. Activity is shown in units/ml (i.e. μmoles of p-nitrophenol/min/ml).

The rate-limiting enzyme of the S. marcescens chitinolytic enzyme ensemble in the hydrolysis of chitin to NAG was evaluated by measuring chitinase and chitobiase activities in batch culture supernatant recovered after 149 hours of induction (see FIG. 7b). pNP (p-nitrophenyl) analogs of chitobiose (substrate for chitobiase) and chitotriose (substrate for chitinase) were used and unit activity for both reactions was taken as $\mu$moles of pNP released per minute. As shown in FIG. 10, chitobiase activity in the supernatant is more than two-fold higher than chitinase, indicating that chitinase activity is rate limiting in the hydrolytic reaction sequence.

Figure 11:
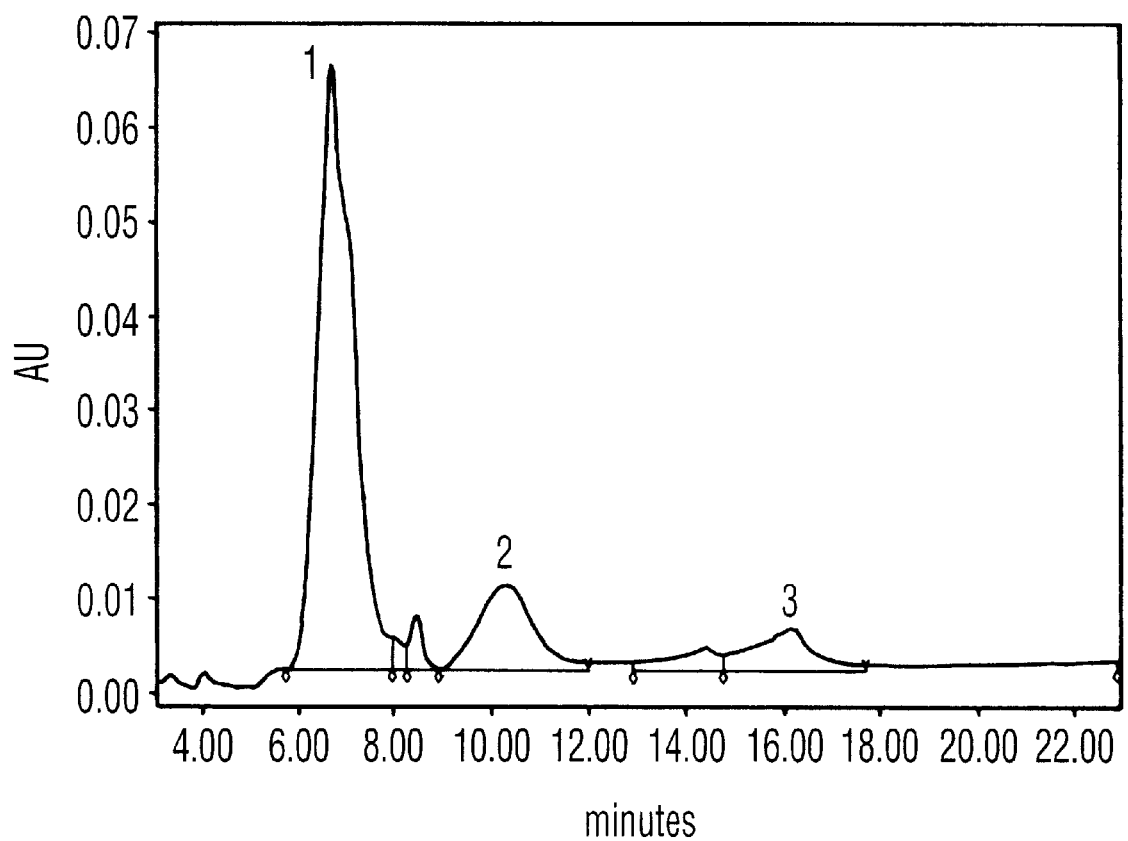
FIG. 11 illustrates HLPC chromatogram of hydrolysis products from swollen colloidal chitin treated with S. marcescens chitinases. 1% swollen chitin was incubated at 37° C. for 2 hr. with an aliquot of S. marcescens supernatant from a 179-hr. culture. The retention times of the different chitooligomers were established by running pure standards. Peak 1: NAG; Peak 2: chitobiose; Peak 3: chitotriose. Peaks were detected by measuring the absorbance at 210 nm.

N-acetyl-D-glucosamine is the end product and the dominant soluble product formed when crab-shell or swollen-colloidal chitin is contacted with culture supernatant at 37° C. and neutral pH. FIG. 11 shows a typical HPLC chromatogram for the soluble hydrolysis products from swollen-colloidal chitin. The first and main peak is N-acetyl-D-glucosamine, constituting ca. 85% of the soluble hydrolysis products, with chitobiose (second peak) and chitotriose (third peak) being the only other products present at significant concentrations. The relatively high N-acetyl-D-glucosamine concentration provides additional evidence that chitinase activity limits the overall hydrolysis rate of the S. marcescens chitinolytic complex on chitin. There is no significant accumulation of any other intermediate product such as chitobiose (15%) or chitotriose (3.7%) which would be expected if the ratio of chitinase vs. chitobiase activity was not in favour of the latter enzyme. This is an important concern for reactor design, since significant accumulation of soluble chitooligomers (chitobiose, chitotriose, etc.) is undesirable and could lead to end-product inhibition of chitinase activity.

Effect of Temperature and pH

Figures 12A, 12B:
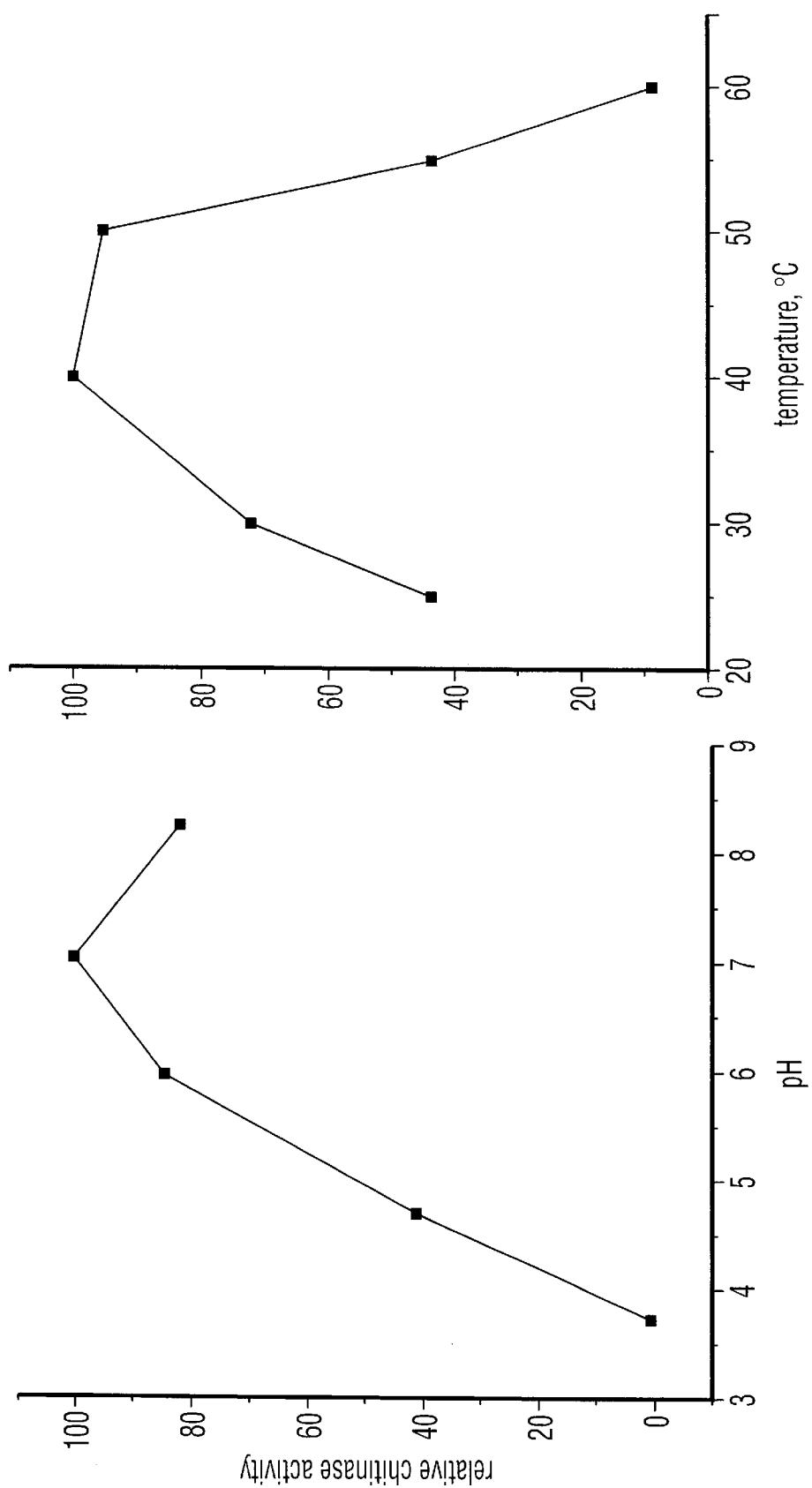
FIGS. 12a and 12b illustrate graphically the respective effects of pH and temperature on chitinase activity. 1 hour reaction, 0.125% swollen, colloidal chitin as substrate, 149-hr. crude extract from S. marcescens culture.

FIG. 12 in the two left and right plots shows the dependence on pH and temperature, respectively, of total chitinase activity, where unit activity now refers to 1 mg of NAG produced per hour, in culture supernatant taken after 149 hours of induction. Trends are the same regardless of whether crab-shell chitin or swollen colloidal chitin are used as substrate. The pH optimum is near neutral, in agreement with earlier studies on different chitin substrates (Monreal and Reese, 1969).

The optimum temperature for chitinase activity is between 40 and 50° C. At temperatures above 50° C. the activity rapidly decreases and is near zero at 60° C. Differential scanning calorimetry data (Calorimetry Sciences Corp. model 7707 heat conduction DSC) of partially purified culture supernatant show that the chitinase enzymes at pH 7 denature near 60° C.

Figure 13B:
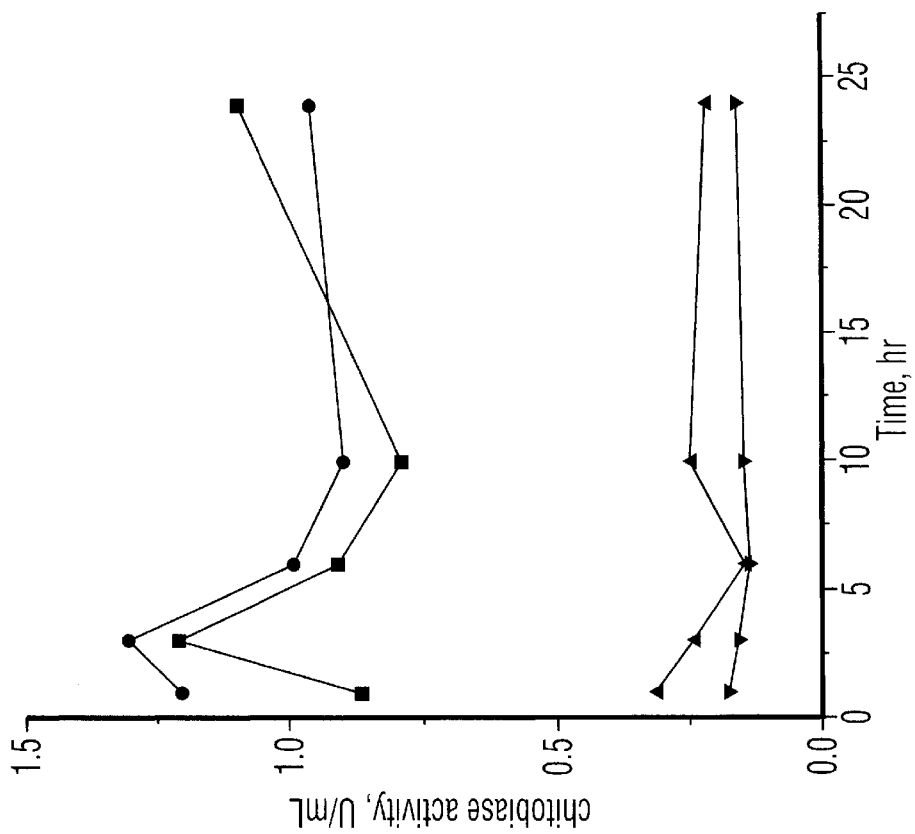
FIGS. 13a and 13b illustrate graphically the stability of chitinases and chitobiase at different temperatures using 149 hr. crude extract from S. marcescens culture.
Figure 13A:
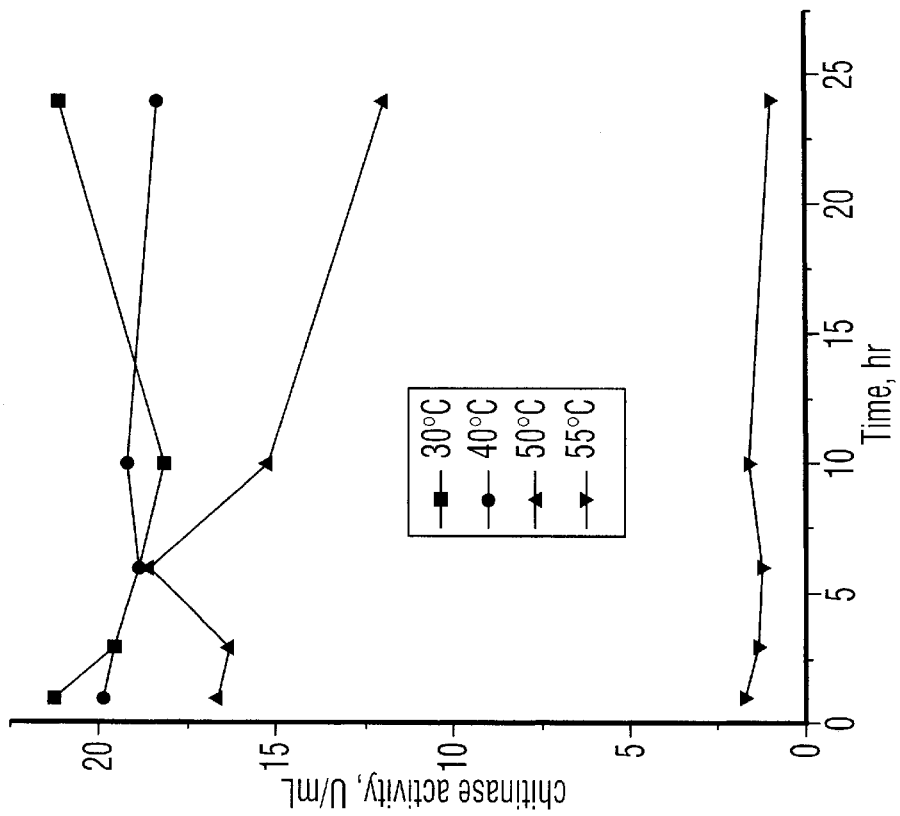

FIG. 13a and FIG. 13b show in two plots the stabilities of chitinase and chitobiase activities in 149-hour culture supernatant at elevated temperatures. For each data point, culture supernatant containing no chitin was incubated at the specified temperature for a period between 1 and 24 hours. Each sample was then assayed at 37° C. for both total chitinase and chitobiase activity. Hydrolytic activities for both enzymes remain high at temperatures of 40° C. and below, and show little to no decrease with time. Incubation of culture supernatant at 50° C. results in a gradual loss in chitinase activity to ca. half its maximum value after 24 hours. At 55° C., which is well within the van't Hoff temperature envelope for thermal denaturation of chitinase (based on the DSC data), activity falls to near zero (ca. 15% of maximum activity). A similar trend is observed for chitobiase, where activity falls to near zero at incubation temperatures at or above the thermal denaturation temperature of ca. 50° C.

Figure 14:
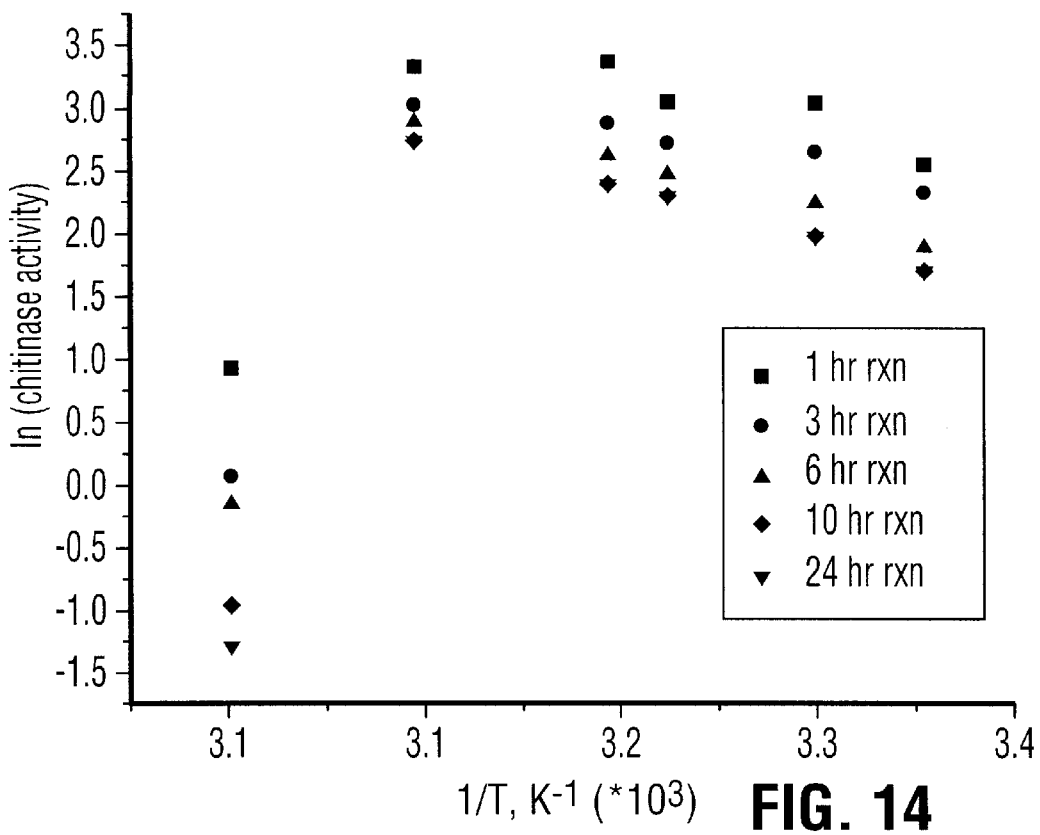
FIG. 14 illustrates an Arrhenius plot for chitin hydrolysis catalyzed by chitinases incubated for different times in colloidal chitin.

In the presence of chitin, which more accurately reflects the actual reactor conditions, the activity of chitinase was measured for a period of 24 hours at temperatures ranging from 30 to 60° C. In this case, activity was assayed at the incubation temperature. Chitin hydrolysis catalyzed by chitinases displays Arrhenius behaviour for temperatures below 50° C. as shown in FIG. 14. The slopes of the Arrhenius plot are approximately the same for the different time points. Since this system represents an ensemble of enzymes nad different reactions, the slope can only give us an effective activation energy for the reaction, $E_{eff}$. From the average value of the slopes, $E_{eff}=374\pm67$ J/mol. The intercepts, which are proportional to the frequency factor of the reaction, decrease with increasing reaction time, indicating end-product inhibition as discussed below.

Enzyme Inhibition

Figure 15A:
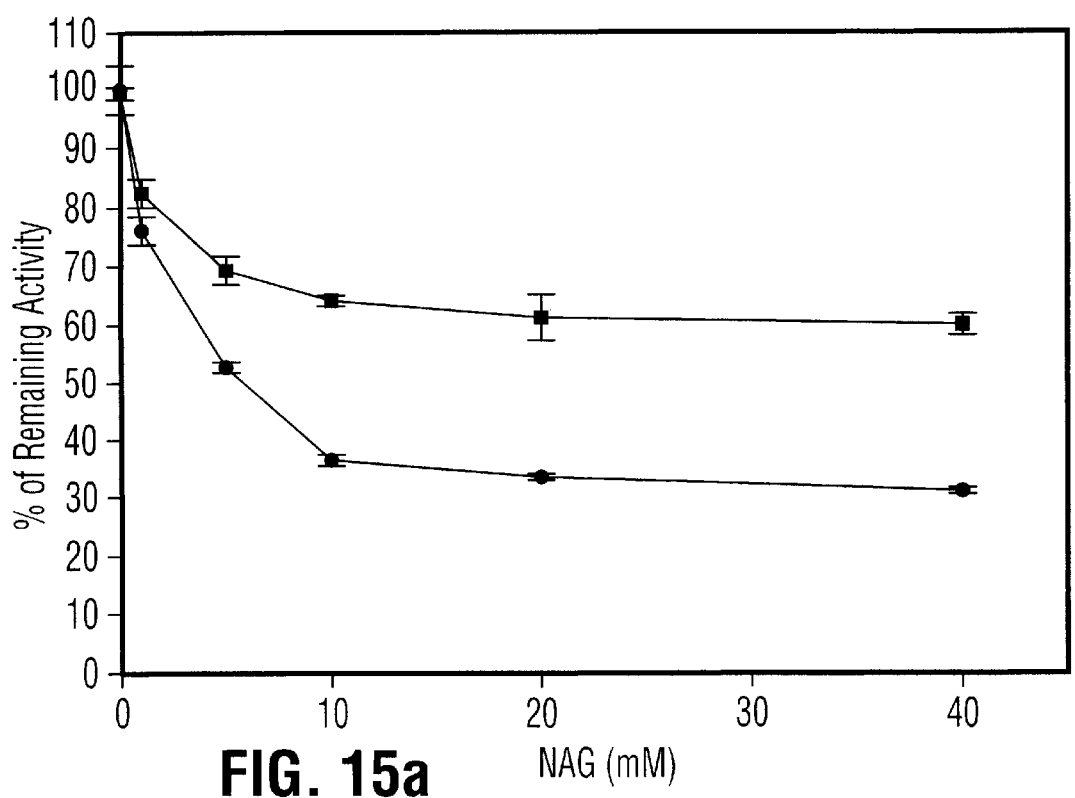
FIG. 15a illustrates assays of chitinase (■) and chitobiase (♦) in the presence of increasing amounts of N-acetyl-D-glucosamine (NAG). The activity values are expressed as percentage of the initial uninhibited values ([NAG]=0).

End-product inhibition was tested using p-nitrophenyl substrate-analogs to assay chitinase and chitobiase activities in the presence of increasing concentrations of N-acetyl-D-glucosamine (NAG). The results shown in FIG. 15a indicate that both activities in culture supernatant are inhibited by the end product (NAG). However, the drop in enzymatic activity for chitobiase is far more significant than that of chitinases. At 40-mM NAG in the assay media, only 30% of total chitinase activity is lost whereas chitobiase activity drops by 70%.

Figure 15B:
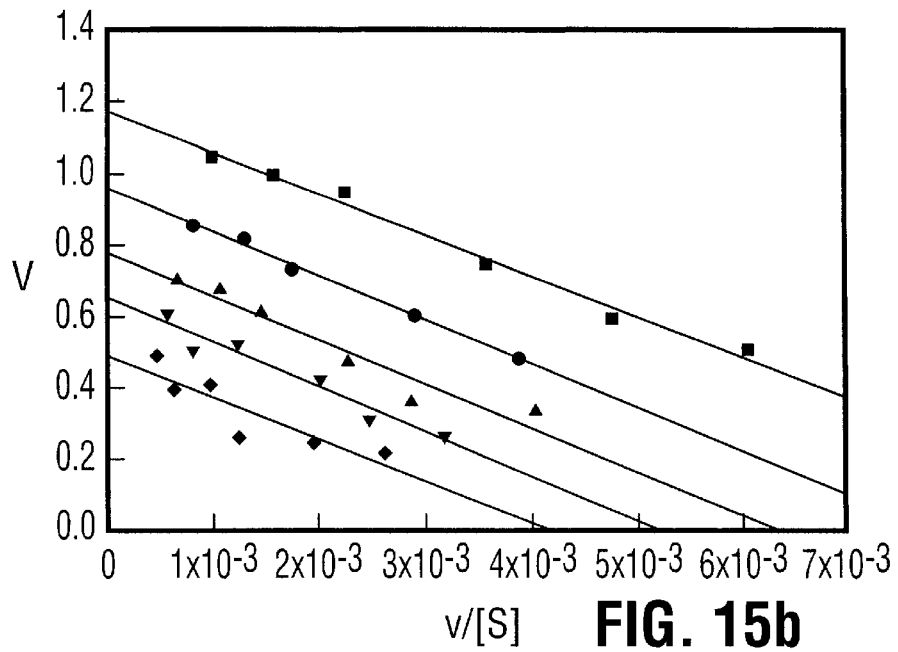
FIG. 15b illustrates assays of chitobiase from S. marcescens crude extracts using a range of p-nitrophenyl N-acetyl-β-D-glucosaminide concentrations with or without the addition of a fixed amount of N-acetyl-D-glucosamine (NAG). (■) 0.00 mM NAG; (●) 0.21 mM NAG; (Δ) 0.42 mM NAG; (∇) 0.83 mM NAG; and (♦) 1.67 mM NAG.

The nature of chitobiase inhibition by N-acetyl-D-glucosamine was determined by assaying chitobiase activity in S. marcescens culture supernatant over a wide range of substrate concentrations, with and without the addition of fixed amounts of N-acetyl-D-glucosamine. Analysis of the resulting Eadie-Hofstee plot (FIG. 15b) indicates noncompetitive inhibition. The $K_m$ is not affected while $V_{max}$ is decreased by increasing concentrations of NAG in the assay media. The inhibition constant $K_i$ calculated from the Eadie-Hofstee analysis is 1.00 (±0.15) mM, indicating that production rates and product purities in the hydrolysis bioreactor will be diminished for reactor conditions where the local NAG concentration exceeds ca. 0.2 g/L. This minimizes the utility of simple bioreactor configurations, such as a one-stage continuous stirred tank reactor (CSTR), and suggests that the optimum reactor configuration will based on the plug-flow reactor scheme, which provides for low initial product concentration and continuous build-up product in the reactor flowstream (e.g. packed-bed reactor or sequential CSTRs).

The nature of chitinase inhibition by N-acetyl-D-glucosamine is more difficult to determine because there is more than one enzyme with chitinase activity produced by S. marcescens when grown on chitin. Although some results remain in question, five different chitinases have been identified in supernatants of S. marcescens cultures (Fuchs et al., 1986). The role of each of these enzymes in chitin hydrolysis is unclear, and little enzymology data is available for any of them in their purified form. However, it is clear from our results (FIG. 15a) that end-product inhibition of chitinase activity is significantly weaker than observed for chitobiase.

This study demonstrates that a cost-effective media for large-scale production of the chitinolytic-enzyme ensemble in Serratia marcescens and the feasibility of using this system for the production of N-acetyl-D-glucosamine from hydrolysis of chitinaceous wastes is practical. The results from this study, combined with an ideal (plug-flow, no fluidization or back mixing) packed-bed reactor model, indicate that a 1000-L bioreactor operated at optimal conditions, and containing 20 U/mL chitinase activity (obtained from our culture supernatant) and an excess of chitin, is capable of producing over half a tonne of N-acetyl-D-glucosamine per day.

The economics of the proposed process will depend on a number of factors, most notably efficient design of the chitin bioreactor such that loss (e.g. inactivation) and inhibition of chitinase and chitobiase activity are minimized. At 40° C., there is essentially no loss of either chitinase and chitobiase activity in S. marcescens culture supernatant over a 24 hour period. However, total chitinase and chitobiase activities are inhibited by the end product N-acetyl-D-glucosamine. This suggests that a one-stage continuous stirred-tank reactor will not be effective, and more sophisticated configurations, such as a packed bed reactor, which produce a gradient in product concentration are required.

TABLE 1

Media Composition for S. marcescens Cultures

| | Concentration (g/L) | |
|---|---|---|
| Component | Minimal Media | Optimized Media |
| Glucose | 2.00 | 0 |
| Chitin | 0 | 15 |
| Yeast Extract | 0 | 0.1 |
| KH$_2$PO$_4$ | 6.80 | 0.136 |
| K$_2$HPO$_4$ | 2.61 | 0 |
| NaCl | 10.00 | 0 |
| (NH$_4$)SO$_4$ | 1.00 | 0 |
| MgSO$_4$.7H$_2$O | 0.123 | 0.15 |
| CaCl$_2$ | 0.0147 | 0 |
| Metal solution* | 1.0% (v/v) | 0 |

*(in 1L distilled H$_2$O: 3.84 g citric acid, 55.6 mg FeSO$_4$.7H$_2$O, 28.7 mg ZnSO$_4$.7H$_2$O, 16.9 mg MnSO$_4$.H$_2$O, 2.5 mg CuSO$_4$.5H$_2$O, 2.5 mg CoCl$_2$, 6.2 mg H$_3$BO$_3$.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

The contents of the following publications are incorporated in this application by reference.
1. Shahidi, F. (1995), Can. Chem. News, 47 (8), 25.
2. Prudden, J. F. (1976) U.S. Pat. No. 4,006,224.
3. Freidman, S. J., and Skehan, P. (1980), Proc. Natl. Acad. Sci. USA, 77, 1172–1176.
4. Cosio, I. G., Fisher, R. A., and Carroad, P. A. (1982), J. Food Sci., 47, 901–905.
5. Zikakis, J. P. (ed.) (1984), Chitin, Chitosan, and Related Enzymes, Academic Press, Orlando.
6. Muzzarelli, R. A. A. (1985), Ch. 6 in: Aspinall, G. O. (ed.) The Polysaccharides, Academic Press, N.Y.
7. Knorr, D. (1991), Food Tech. 45, 114–122.
8. Cody, R. M., Davis, N. D., Lin, J., and Shaw, D. (1990), Biomass. 21, 285–295.
9. Annual Report, Pfanstehl Chemicals, Chicago Ill. (1992).
10. Roberts, R. L., and Cabib, E. (1982), Anal. Biochem. 127, 402–412.

11. Schlumbaum, A., Mauch, F., Vogeli, U., and Boller, T. (1986), *Nature*, 324, 365–367.
12. Gooday, G. W. (1989), p. 13–22 in: Skjåk-Braek, G., Anthonsen, T., Sanford, P. (eds.) *Chitin and Chitosan*, Elsevier Applied Science, London.
13. Gilkes, N. R., Jervis, E., Henrissat, B., Tekant, B., Miller Jr., R. C., Warren, R. A. J., and Kilburn, D. G. (1992), *J. Biol. Chem.*, 267, 6743.
14. Gilkes, N. R., Henrissat, B., Kilburn, D. G., Miller Jr., R. C., and Warren, R. A. J. (1991), *Microbiol. Rev.*, 55, 303.
15. Gilkes, N. R., Warren, R. A. J., Miller Jr., R. C., and Kilburn, D. G. (1988), *J. Biol. Chem.*, 263, 10401.
16. Ong, E., Gilkes, N. R., Miller Jr., R. C., Warren, R. A. J., and Kilburn, D. G. (1991), *Enzyme Microb. Technot.*, 13, 59.
17. Coutinho, J. B., Gilkes, N. R., Warren, R. A. J., Kilburn, D. G., and Miller Jr., R. C. (1992), *Mol. Microbiol.*, 6, 1243.
18. Greenwood, J. M., Gilkes, N. R., Henrissat, B., Kilburn, D. G., Miller Jr., R. C., and Warren, R. A. J. (1989), *FEBS Lett.*, 244, 127.
19. Monreal, J., and Reese, E. T. (1969), *Can. J. Microbiol.*, 15, 689–696.
20. Neugebauer, E., Gamache, G., Déry, C. V., and Brzezinski, R. (1991), *Arch. Microbiol.*, 156, 192–197.
21. Ulhoa, C. J., and Peberdy, J. F. (1992), *Enzyme Microb. Technol.*, 14, 236–240.
22. Vyas, P., and Deshpande, M. V. (1989), *J. Gen. Appl. Microbiol.*, 35, 343–350.
23. Reynolds, D. M. (1954), *J. Gen. Microbiology*, 11, 150.
24. Berger, L. R., Reynolds, D. M. (1958), *Biochim. Biophys. Acta*, 29, 522.
25. Rupley, J. A. (1964), *Biochim. Biophys. Acta*, 83, 245.
26. Mateles, R. I. , Battat, E. (1974), *Appl. Microbiol.*, 28, 901.
27. Fuchs, R. L., McPherson, S. A., and Drahos, D. J. (1986), *Appl. Environ. Microbiol.*, 51, 504–509.
28. Johnson, L. N. (1964), *Nature*, 202, 588.
29. Mori, H., Yano, T., Kobayashi, T., and Shimizu, S. (1979), *J. Chem. Eng. Jap.*, 12, 313.
30. Sigma Chemical Co., St. Louise Mo.
31. Robbins, P. W., Albright, C., and Benfield, B. (1988), *J. Biol. Chem.*, 263, 443–447.
32. Reid, J. D., and Ogrydziak, D. M. (1981), *Appl. Environ. Microbiol*, 41, (3) 664–669.
33. Horwitz, M., Reid, J., and Ogrydziak, D. (1984), p. 191–208 in: Zikakis, J. P. (ed.) *Chitin, Chitosan, and Related Enzymes*, Academic Press, Orlando.
34. Joshi, S., Kozlowski, M., Richens, S. and Comberbach, D. M. (1989), *Enzyme Microb. Technol.*, 11, 289–296.
35. Zhu, B. C. R., Lo, J.-Y., Li, Y.-T., Li, S.-C., Jaynes, J. M., Gildemeister, O. S., Laine, R. A., and Ou, C.-Y. (1992), *J. Biochem.*, 112, 163–167.
36. Vasseur, V., Arigoni, F., Anderson, H., Defago, G., Bompeix, G., and Seng, J.-M. (1990), *J. Gen. Microbiol.*, 136, 2561–2567.
37. Tom, R. A., and Carroad, P. A. (1981), *J. Food Sci.*, 46, 646–647.
38. Sabry, S. A. (1992), *J. Basic Microbiol.*, 32, 107.

What is claimed is:

1. A process for producing N-acetyl-D-glucosamine by enzymatically hydrolyzing chitin with chitinolytic, which consists essentially of:
   (a) introducing a chitin-containing solid, a carbohydrate-free media, and a microorganism which produces chitin-degrading and chitobiose-degrading enzymes when grown on chitin into a first culture fermentor vessel;
   (b) producing a fermentation broth culture in the first culture fermentor vessel by applying a culturing protocol which induces the microorganism to produce and secrete chitinolytic enzymes containing at least one chitin-degrading enzyme, which is chitinase, and one chitobiose-degrading enzyme, which is chitobiase, which are secreted by the microorganism to the extracellular fluid;
   (c) separating the chitinolytic enzymes as a filtrate from other components of the fermentation broth culture which has been formed in the first culture fermentor vessel;
   (d) introducing the separated chitinolytic enzymes filtrate and chitin-containing solids into a two-stage, packed bed and solids-free volume chitin-hydrolysis reactor separate from the first culture vessel for sufficient residence time wherein the chitin in the solids is hydrolyzed by the chitinase and the chitobiase in the chitinolytic enzymes to N-acetyl-D-glucosamine;
   (e) separating the N-acetyl-D-glucosamine which has been formed in the second reactor into a filtrate stream and the chitinolytic enzymes in the second reactor into a retentate stream; and
   (f) recovering the N-acetyl-D-glucosamine from the filtrate stream.

2. The process as claimed in claim 1 wherein the chitinolytic enzymes contain at least one chitinase and one chitobiase produced and secreted from either a procaryotic or eucaryotic microorganism.

3. The process as claimed in claim 2 wherein the chitinase is either an endo- or exo-β-1,4-glycanohydrolase, and the chitobiase is a β-n-acetyl-glucosaminidase, or a β-N-acetyl-hexosaminidase.

4. The process as claimed in claim 1 wherein the chitin-containing solid is selected from the group consisting of the exoskeletons of krill, shrimp, crab and lobster.

5. The process as claimed in claim 2 wherein the procaryotic microorganism is a bacterial cell line selected from the group consisting of *Serratia marcescens, Streptomyces lividans* and *Enterobacter liquefaciens*.

6. The process as claimed in claim 2 wherein the eucaryotic microorganism is a fungal cell line selected from the group consisting of *Trichoderma harzianum* and *Myrothecium verrucaria*.

7. The process as claimed in claim 1 wherein the chitinolytic enzymes in step (e) are concentrated by two-step cross-flow filtration.

8. The process as claimed in claim 7 wherein the process is conducted at a pH between about 5.5 and 8 and at a temperature between about 25° C. and 55° C.

9. The process as claimed in claim 1 wherein the chitinolytic enzymes are produced by introducing an inoculum of a procaryotic or eucaryotic microorganism into the first culture fermentor vessel to induce production of enzymes having chitinase or chitobiase activity; and recovering chitin-degrading enzymes or chitobiose-degrading enzymes from the culture.

10. The process as claimed in claim 9 wherein the chitinolynic enzymes in step (c) are separated by passing the culture through a membrane separator to yield a filtrate solution containing the chitinolytic enzymes as a first component and a second retentate containing viable cells and chitin as a second component.

11. The process as claimed in claim 9 wherein the enzymes in step (c) are recovered by passing the culture through a centrifuge to yield a filtrate solution containing the chitinolytic enzymes as a first component and a second retentate containing viable cells and chitin as a second component.

12. The process as claimed in claim 10 wherein the second retentate from the membrane separator is recycled to the first culture fermentor vessel.

13. The process as claimed in claim 11 wherein the second retentate from the centrifuge is recycled to the first culture fermentor vessel.

14. The process as claimed in claim 1 wherein the retentate of chitinolytic enzymes in step (e) comprising chitinase and chitobiase are recycled to the second chitin-hydrolysis reactor.

15. The process as claimed in claim 1 wherein the second two-stage reactor of step (d) comprises a single unit having a bottom portion and an upper portion, the bottom portion containing a packed-bed of chitin-containing solid through which a chitinolytic enzyme-containing mobile phase can pass and the upper portion containing a solids-free aqueous solution containing chitobiose-degrading enzyme.

16. The process as claimed in claim 1 wherein the second two-stage reactor of step (d) comprises a first reactor containing a packed-bed of chitin-containing solid through which an enzyme-containing mobile phase can pass and a second reactor connected to the first reactor, the second reactor being a stirred tank containing a solids-free aqueous solution which is catalyzed by one or more chitobiose-degrading enzymes.

17. The process as claimed in claim 15 wherein the enzyme containing mobile phase is introduced into the bottom of the packed bed.

18. The process as claimed in claim 15 wherein the two-stage reactor is maintained at a pH of between about 5.5 and 7.5, and an isothermal temperature of between about 30° C. and 55° C.

19. The process as claimed in claim 1 wherein the chitin-containing solids of steps (a) and (d) are pre-treated to increase external surface area of chitin.

20. The process as claimed in claim 19 wherein the pretreatment comprises ballmilling or hammer-milling of the chitin-containing solids.

21. The process as claimed in claim 19 wherein the pretreatment comprises steam explosion or steam expansion of the chitin-containing solids.

22. The process as claimed in claim 1 wherein the chitinolytic enzymes and the N-acetyl-D-glucosamine in step (e) are separated into a filtrate stream and a retentate stream by an ultrafiltration process.

23. The process as claimed in claim 1 including mechanically or physio-chemically treating the chitin-containing solids in the other components of the culture in step (c) before introducing the chitin containing solids into the second chitin-hydrolysis reactor of step (d).

24. The process as claimed in claim 23 wherein the chitinolytic enzymes in the retentate stream of step (e) comprising chitinase and chitobiase are recycled to the second chitin-hydrolysis reactor of step (d).

* * * * *